(12) United States Patent
Nieland et al.

(10) Patent No.: US 7,528,168 B2
(45) Date of Patent: May 5, 2009

(54) INHIBITORS OF THE FATTY ACID OXIDATION FOR THE PROPHYLAXIS AND/OR THE TREATMENT OF CHRONIC AND/OR ATOPIC SKIN DISEASES

(75) Inventors: John Nieland, Scheideggerstrasse 31, Münich (DE) 81476; Irene Gander-Meisterernst, Stockdorf (DE); Martin Rohrbach, München (DE); Barbara Nave, München (DE)

(73) Assignee: John Nieland, Aarhus (DK)

( * ) Notice: Subject to any disclaimer, the term of this patent is extended or adjusted under 35 U.S.C. 154(b) by 309 days.

(21) Appl. No.: 10/528,308

(22) PCT Filed: Sep. 18, 2003

(86) PCT No.: PCT/EP03/10397

§ 371 (c)(1),
(2), (4) Date: Sep. 12, 2005

(87) PCT Pub. No.: WO2004/026405

PCT Pub. Date: Apr. 1, 2004

(65) Prior Publication Data

US 2006/0089406 A1 Apr. 27, 2006

Related U.S. Application Data

(60) Provisional application No. 60/411,962, filed on Sep. 19, 2002.

(51) Int. Cl.
*A61K 31/336* (2006.01)
*A01N 43/20* (2006.01)
(52) U.S. Cl. .................. 514/475; 514/449; 424/400

(58) Field of Classification Search ............... None
See application file for complete search history.

(56) References Cited

U.S. PATENT DOCUMENTS 4,933,365 A * 6/1990 Marshall et al. ............. 514/475
4,935,450 A     6/1990 Cone, Jr.

FOREIGN PATENT DOCUMENTS

WO    WO 02/056022 A2    7/2002
WO    WO 03/063810 A2    8/2003

OTHER PUBLICATIONS

Definition of prevent from dictionary.com, accessed Nov. 28, 2007.*
Madsen et al. J Invest Dermatol, 99, p. 299-305 (1992).*
Spurway et al. FEBS Letters 404, p. 111-114 (1997).*
F. Caspary et al., "A New Therapeutic Approach to Treat Psoriasis by Inhibition of Fatty Acid Oxidation by Etomoxir," *British Journal of Dermatology* 153:937-944 (2005).
Lau et al., "Amiodarone: A new treatment for psoriasis?" *British Medical Journal*. 293: p. 510 (1986).
Hollman, "Amiodarone: A new treatment for psoriasis?" *British Medical Journal*. 293: p. 823 (1986).

* cited by examiner

*Primary Examiner*—Michael G Hartley
*Assistant Examiner*—Nissa M Westerberg
(74) *Attorney, Agent, or Firm*—Clark & Elbing LLP

(57) ABSTRACT

The invention relates to a method of preventing and/or treating a chronic and/or an atopic skin disease by administering an inhibitor of fatty acid oxidation to a patient in a pharmacologically effective amount. Furthermore, the invention relates to the use of at least one inhibitor of fatty acid oxidation for the preparation of a pharmaceutical composition for the prophylaxis and/or treatment of a chronic and/or an atopic skin disease.

6 Claims, 21 Drawing Sheets

INHIBITORS OF THE FATTY ACID OXIDATION FOR THE PROPHYLAXIS AND/OR THE TREATMENT OF CHRONIC AND/OR ATOPIC SKIN DISEASES

CROSS REFERENCE TO RELATED APPLICATIONS

This application is the U.S. National Stage of International Application No. PCT/EP2003/010397, filed Sep. 18, 2003, which claims benefit of U.S. Provisional patent application 60/411,962, filed Sep. 19, 2002.

The present invention refers to the identification of therapeutic methods and pharmaceutical compositions for the prophylaxis and/or the treatment of chronic and/or atopic skin diseases, especially proliferative skin diseases.

The skin is the main protective barrier of the body against external influences. It is composed of the epidermis and the dermis, wherein the epidermis is subdivided into five layers or strata, the stratum germinativum (SG), the stratum spinosum (SS), the stratum granulosum (SGR), the stratum lucidum and the stratum corneum (SC).

A main component of the layers of the epidermis are fatty acids. Skin contains free fatty acids as well as fatty acids bound in triglycerides, phospholipids, glycosylceramides and ceramides (sphingolipids). The epidermal keratinocyte, the main cell type in the epidermis, is highly active in the synthesis of said several lipids. Fatty acids and their derivatives are part of the intercellular stratum corneum lipid bilayers which regulate the cutaneous permeability barrier.

In western countries, many people are affected by skin diseases. A large proportion thereof involve reddening of the skin (erythema) and peeling of the skin (desquamation). The erythema is the cardinal symptom of inflammation. If inflammation extends to the uppermost layer of the dermis, i.e., to the vascular connective tissue situated immediately below the epidermis (top skin layer), epidermal changes will ensue. Initially the epidermis may thicken resulting in acanthosis. If inflamed the skin is penetrated by fluid and inflammatory cells, vesicles and pustules develop, eventually leading to scaling of the top skin layers, i.e. desquamation and reddening of skin.

A common disorder with this feature is psoriasis. Psoriasis affects 0.2-3% of the population. Psoriasis is a chronic skin disease that generally appears as patches of raised red skin covered by a flaky white. buildup. Psoriasis most often affects the extensor surface of the extremities especially the arms and elbows. Other areas that can be involved include the side and back of scalp, the perianal region, the extensor surfaces of the interphalangeal finger joints (where the lesions resemble calluses) and the finger and toe nails, but also other parts of the body surface can be affected. Furthermore, intestinal mucosal changes occur in psoriasis.

Psoriasis can appear in several forms, such as plaque psoriasis, guttate psoriasis, inverse psoriasis, erythrodermic psoriasis, generalized pustular psoriasis or localized pustular psoriasis, whereby plaque psoriasis is the most common type.

Although the exact cause is unknown, psoriasis is believed to be related to faulty signals sent by the body's immune system. These signals accelerate the growth cycle in skin cells, which pile up on the surface when the body can't shed them fast enough. Instead of normal cornification, the mitotic rate (cell division rate) in the epidermis increases to seven times its normal level with formation of a pathological stratum corneum. Due to the fact that the cells have no time to mature, said over-proliferation results in scaling.

Psoriasis can range from mild to moderate to very severe and disabling. Attacks of psoriasis are normally triggered by stress, trauma, food allergies, essential fatty acid deficiencies, liver congestion, constipation, low stomach acid levels, Vitamin B deficiencies, illness, alcohol consumption, damage to the skin or infection with pathogens like yeast, fungal or bacteria. Currently, there is no cure for psoriasis.

Accordingly, it is the object of the present invention to provide therapeutic approaches and pharmaceutical compositions which are useful in the prophylaxis and/or the treatment of said skin conditions.

In a first aspect of the invention, the problem is solved by a method of preventing and/or treating a chronic and/or an atopic skin disease by administering an inhibitor of fatty acid oxidation to a patient in a pharmacologically effective amount.

The present invention is based on the unexpected finding that the inhibition of the oxidation of fatty acids elicits a positive effect on chronic and/or atopic, especially proliferative skin diseases.

Consequently, the present invention provides for the first time the possibility to prevent, alleviate or cure said skin diseases.

Without being bound to any theory, it is believed that in diseased skin the produced fatty acids are oxidized and used as an energy source instead of being used for skin formation and barrier function. As mentioned above said skin diseases are associated with an increased cell division rate and therefore an increased energy demand met probably via increased fatty acid oxidation. The increased catabolism of fatty acids may lead to a lack of fatty acids for the assimilation in skin formation. Furthermore the increased fatty acid oxidation means an increase in the formation of reactive oxygen radicals which play a role in inflammatory processes.

As used herein, the terms "inhibitor" or "inhibiting agent" refer to any compound capable of down-regulating, decreasing, reducing, suppressing, or inactivating the amount and/or activity of an enzyme, particularly the enzymes involved in fatty acid oxidation referred to below. Generally, these inhibitors or inhibiting agents may be proteins, oligo- and polypeptides, nucleic acids, genes, and chemical molecules. Suitable protein inhibitors may be, for example, monoclonal or polyclonal antibodies which bind to one of the enzymes described below. Inhibition of enzymes can be achieved by any of a variety of mechanisms known in the art, including, but not limited to, binding directly to the enzyme (e.g., enzyme inhibitor compound binding complex or substrate mimetic), denaturing or otherwise inactivating the enzyme, inhibiting the expression of a gene which encodes the enzyme (e.g., transcription to mRNA, translation to a nascent polypeptide) and/or final modifications to a mature protein.

As used herein, the term "inhibit" or "inhibiting" refer to any effect in down-regulating, decreasing, reducing, suppressing, or inactivating (also partially) the amount and/or activity of an enzyme, particularly the enzymes involved in fatty acid oxidation referred to below.

As used herein, the term "regulating the expression and/or activity" generally refers to any process that functions to control or modulate the quantity or activity (functionality) of a cellular component, particularly an enzyme. Static regulation maintains expression and/or activity at some given level. Up-regulation refers to a relative increase in expression and/or activity. Accordingly, down-regulation refers to a decrease in expression and/or activity. Down-regulation is synonymous with the inhibition of a given cellular component's expression and/or activity.

As used herein, a "pharmaceutically effective amount" of an inhibitor is an amount effective to achieve the desired physiological result, either in cells treated in vitro or in a subject treated in vivo. Specifically, a pharmaceutically effective amount is an amount sufficient to inhibit, for some period of time, one or more clinically defined pathological effects associated with the chronic or atopic skin diseases. The pharmaceutically effective amount may vary depending on the specific inhibitor selected, and is also dependent on a variety of factors and conditions related to the subject to be treated and the severity of the disease. For example, if the inhibitor is to be administered in vivo, factors such as age, weight, sex, and general health of the patient as well as dose response curves and toxicity data obtained in pre-clinical animal tests would be among the factors to be considered. If the inhibitor is to be contacted with cells in vitro, one would also design a variety of pre-clinical in vitro studies to asses parameters like uptake, half-life, dose, toxicity etc. The determination of a pharmaceutically effective amount for a given agent (inhibitor) is well within the ability of those skilled in the art. Preferably, the inhibitor is present in a concentration of 0,1 to 50% per weight of the pharmaceutical composition, more preferably 10 to 30%.

Administration to an individual may be in a single dose or in repeated doses. Repeated doses are preferred, especially once or twice a day until the lesions disappear.

Suitable inhibitors can be identified by screening test compounds, or a library of test compounds, for their ability to inhibit the fatty acid oxidation of cells, particularly to inhibit enzymes involved in the fatty acid oxidation. In this context, cells or cell lysates are tested for their ability to degrade palmitate by incubating the cells or cell lysates with radioactive palmitate and measuring the production of radioactive ketone bodies and/or the release of $^{14}CO_2$. Furthermore, it is possible to perform an in silico screen, based on the structure of a known enzyme invoved in fatty acid oxidation. Additionally, the substrate processing of a purified enzyme, e.g. an enzyme involved in β-oxidation, could be measured (Rubi, B. et al., *Biochem. J.* (2002) 364, 219-226).

The patient to be treated with the methods of the present invention is preferably human. However, also animals, preferably mammals as horses, bovines, dogs or cats and more preferably primates can be treated according to the present invention.

According to a preferred embodiment of the present invention, the inhibitor inhibits the expression and/or activity of the enzyme Carnitin-Palmitoyl-Transferase-1 (CPT-1), which is a key enzyme of the fatty acid oxidation pathway.

More preferably, the inhibitor inhibiting the expression and/or activity of the enzyme Carnitin-Palmitoyl-Transferase-1 (CPT-1) is an arylalkyl- and aryloxyalkyl-substituted oxirane carboxylic acid of the following formula I

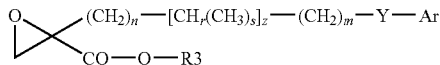

wherein
Ar is a substituted phenyl radical

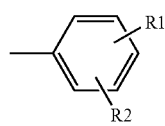

a 1- or 2-naphthyl radical which is substituted by a radical R4, or
a heterocyclic radical Het;

R1 is a hydrogen atom, a halogen atom, or a 1-4 C lower alkyl group; a 1-4 C lower alkoxy group, a nitro group, or a trifluoromethyl group;

R2 is a hydrogen atom, a halogen atom, or a 1-4 C lower alkyl group; a 1-4 C lower alkoxy group, a nitro group, a trifluoromethyl group, a fully or predominantly fluorine-substituted 1-3 C alkoxy group or one of:

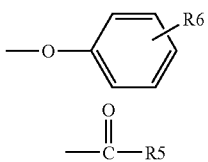 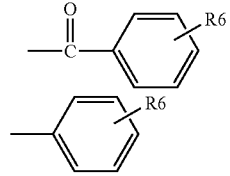

R3 is a hydrogen atom or a 1-4 C lower alkyl group;
R4 is a hydrogen atom, a 1-4 C lower alkyl group, an optionally fully or predominantly fluorine-substituted (i.e. more fluor than hydrogen atoms are present) 1-3 C alkoxy group, or a halogen atom;
R5 is a 1-4 C lower alkyl group;
R6 is a hydrogen atom, a halogen atom, or a 1-4 C lower alkyl group;
Y is the grouping —O— or —$CH_2$—;
z is 0 or 1
s is 1 or 2
r is 2-s
n and m are an integer $\geq 0$ with $2 \leq n+m \leq 8$; and
Het is a heterocyclic ring, which preferably has 5 members and is selected from the group consisting of thiophene, thiazole, isothiazole, pyrrole, and, particularly preferably, pyrazole, and which may carry 1 or 2 identical or different substituents R1;

as well as pharmaceutically acceptable salts and derivatives of said arylalkyl- or aryloxyalkyl-substituted oxirane carboxylic acid. Preferred derivatives are the alkyl esters of the arylalky- and aryloxyalkyl-substituted oxirane carboxylic acids, especially the ethyl esters.

Particularly useful inhibitors which fall under formula I above are 2-(6-(4-chlorophenoxy)hexyl)oxirane-2-carboxylic acid ethyl ester (Etomoxir), 2-(6-(4-difluoromethoxyphenoxy)hexyl)-oxirane-2-carboxylic acid ethyl ester, 2-(5-(4-difluoromethoxyphenoxy)pentyl)-oxirane-2-carboxylic acid ethyl ester, and 2-(5-(4-acetylphenoxy)pentyl)-oxirane-2-carboxylic acid ethyl ester, Etomoxir being especially preferred.

Other useful CPT-1 inhibitors are sodium-2-(5-(4-chlorophenyl)pentyl)-oxirane-2-caboxylate (Clomoxir), Perhexiline, sodium-4-hydroxyphenylglycine (Oxfenicine), 2-tetradecylglycidate (TDGA), Palmoxirate, Amiodarone, and derivatives thereof (Deschamps D et al., *Hepatology* 1994 April; 19(4):948-61; Kennedy J A et al., *Biochem Pharmacol* 1996 Jul. 26;52(2):273-80; Carregal M et al., *Arch Physiol Biochem* 1995 April; 103(1):45-9; Kennedy J A et al., *J Cardiovasc Pharmacol* 2000 December; 36(6):794-801; Swithers S E, *Am J Physiol* 1997 November; 273(5 Pt2):R1649-56; Friedman M I et al., *Am J Physiol* 1990 January; 258(1 Pt 2):R216-21; Seitelberger R et al., *J Clin Chem Clin Biochem* 1990 May; 28(5):341-6; Reinauer H et al., *J Clin Chem Clin*

*Biochem* 1990 May; 28(5):335-9; Skorin C et al., *Biochem J* 1992 Jan. 15;281(Pt 2):561-7; Tuman R W et al., *Int J Biochem* 1988;20(2):155-60).

Furthermore, CPT-1 inhibition can be achieved by use of a factor which increases intracellular levels of Malonyl-CoA, since Malonyl-CoA is a physiologic inhibitor of CPT-1 (Prip-Buus C et al., *Biochem J* 1990 Jul. 15;269(2):409-15; Winder W W, *Exerc Sport Sci Rev* 1998;26:117-32; Lopaschuk G D & Gamble J, *Can J Physiol Pharmacol* 1994 October; 72(10): 1101-9).

Consequently, in a preferred embodiment, the inhibitor is a factor which increases the Malonyl-CoA-levels in the patient.

Suitable factors for increasing the Malonyl-CoA level can be preferably selected from the group consisting of an activator of the Acetyl-CoA-Carboxylase, an inhibitor of the AMP-Kinase, an inhibitor of the Citrate synthase, an inhibitor of the Fatty Acid Synthase or an inhibitor of the Malonyl-CoA-Decarboxylase. Cerulenin as well as the compound C75 are known to be Fatty Acid Synthase inhibitors causing an increase in Malonyl-CoA-levels (Pizer E S et al., *Cancer Research* 60, 213-218, Jan. 15, 2000; Thupari J N et al., *Biochem Biophys Res Commun* 2001 Jul. 13;285(2):217-23).

Another option to decrease the fatty acid oxidation is to inhibit the fatty acid binding protein(s) (FABP) which is/are responsible for the binding and transportation of free fatty acids through the cytoplasm of a cell to the mitochondria (Burczynski F J et al., *Can J Physiol Pharmacol* 1999 November; 77(11):896-901; Glatz J F et al., *J Mol Neurosci* 2001 April-June; 16(2-3):123-32).

Consequently, in a preferred embodiment, the inhibitor inhibits the expression and/or activity of at least one isoform of a fatty acid binding protein (FABP).

An especially preferred isoform which expression and/or activity is to be inhibited is the psoriasis associated FABP (PA-FABP), also known as cutaneous FABP (C-FABP), epidermal FABP (E-FABP) or FABP-5.

In a further preferred embodiment, the inhibitor which inhibits the expression and/or activity of at least one isoform of a fatty acid binding protein (FABP) is a substance which binds to FABP.

Examples for such substances which bind to FABP are fluorescent fatty acid derivatives. For example, cis-parinaric acid (cPA) can be noted which has been reported for measurement of ligand binding affinities of different FABPs (see e.g. Sha, R. S. et al., 1993). A second inhibitor is 12-(anthroyloxy)-oleic acid (12-AO). A third inhibitor is 8-anilino-naphthalene-1-sulfonic acid (ANS). ANS has been described in the context of a displacement assay with FABPs (Kane C. D. et al., 1996), and a structure of A-FABP in complex with ANS has been published (Ory J. J. et al., 1999).

In a further embodiment, the inhibitor may inhibit the expression and/or activity of any enzyme involved in the fatty acid oxidation.

Such enzymes are, besides the above-mentioned CPT-1, preferably selected from the group consisting of Phospholipase A, Lipoproteinlipase, Hormone sensitive Lipase, Monoacylglycerol-Lipase, Acyl-CoA-Synthetase, Canitin-Acylcamitin-Translocase, Carnitin-Palmitoyl-Transferase-2 (CPT-2), Acyl-CoA-Dehydro-genase, Enoyl-CoA-Hydratase, L-3-Hydroxyacyl-CoA-Dehydrogenase, or 3-Ketoacyl-CoA thiolase (3-KAT).

Useful inhibitors of these enzymes involved in the fatty acid oxidation are, for example, trimetazidine, which is known as a 3-Ketoacyl-CoA thiolase (3-KAT)-inhibitor and ranolazine, which is supposed to be an Enoyl-CoA-Hydratase-inhibitor (Spedding M et al., *Therapie* 1999 September-October; 54(5):627-35; Kantor P F et al., *Circ Res* 2000 Mar. 17;86(5):487-9; Zacharowski K et al., *Eur J Pharmacol* 2001 Apr. 20;418(1-2):105-10; Goldschmidt M & Frishman W H, *Am J Ther* 1995 April; 2(4):269-274).

Furthermore, the inhibitor may be an antisense oligonucleotide or a dominant negative mutant of any enzyme involved in the fatty acid oxidation, particularly the enzymes CPT-1, Acetyl-CoA-Carboxylase, Phospholipase A, Lipoprotein-lipase, Hormone sensitive Lipase, Monoacylglycerol-Lipase, Acyl-CoA-Synthetase, Canitin-Acylcarnitin-Translocase, CPT-2, Acyl-CoA-Dehydrogenase, Enoyl-CoA-Hydratase, L-3-Hydroxyacyl-CoA-Dehydrogenase, or 3-Ketoacyl-CoA thiolase (3-KAT). Besides antisense oligonucleotides and dominant negative mutants of any enzyme involved in the fatty acid oxidation, also ribozymes and dsRNA can be used as inhibitors of fatty acid oxidation in the context of the present invention. Furthermore, any combination of one or more antisense oligo-nucleotide, ribozyme and/or dsRNA with one or more antisense oligonucleotide, ribozyme and/or dsRNA can be used according to the present invention.

The effect of antisense oligonucleotides, ribozymes and dsRNA is due to sequence-specific interactions with the RNA coding for the respective protein. Thereby the structure and/or function of coding RNA sequences are modified in a way that the expression of the originally encoded protein or the effect of the RNA is decreased or completely blocked. Furthermore, this mechanism results in an enzymatic degradation of the RNA. Thus, those mechanisms work on the basis of inhibiting the production of the target protein itself rather than blocking its function.

The invention includes also the administration of a combination of the above inhibitors. Particularly, effective combinations of fatty acid oxidation inhibitors can be the simultaneous use of a CPT-1 inhibitor and a FABP inhibitor, or the simultaneous use of a CPT-1 and CPT-2 inhibitor.

Chronic or atopic skin diseases which can be treated according to the invention are, for example, psoriasis, cutaneous atopy (e.g. eczema), dermatitis, hand dermatitis, Darrier's disease, xerosis, rosacea, seborrhea, ichthyosis, pigmentation disorders (e.g. hyperpigmentation, melasma, hypopigmentation or vitiligo), actinic keratosis, hyperkeratosis, mycosis fungoides, lichen planus, hyperplasia of the epidermis and other diseases related to inflammatory processes and/or increased proliferation of skin cells.

The administration of the inhibitor is not limited to a specific route. Preferred routes of administration to an individual include but are not limited to parenteral, especially dermal, intradermal, intracutaneous, percutaneous, subcutaneous, topical or transdermal application.

In an especially preferred embodiment of the invention the inhibitor is administered topically. The inhibitor may be administered in the form of salves, creams, emulsions, milks, ointments, powders, impregnated pads, solutions, gels, sprays, lotions or suspensions. Moreover, the inhibitor may be administered in the form of shampoo, conditioner, hair tonic, hair spray, hair foam, hair paste or fixature. Same can also be administered in the form of lipid or polymeric microspheres or nanospheres or vesicles or of polymeric patches and hydrogels which permit controlled release.

In a further preferred embodiment, the inhibitor inhibits fatty acid oxidation in the epidermis.

In a further preferred embodiment, the inhibitor inhibits fatty acid oxidation in the dermis, more preferably in the epidermis and dermis.

In a further embodiment said prevention and/or treatment of a chronic or an atopic skin disease comprises the administration of an inhibitor of the fatty acid oxidation in combination with a further therapy. This may result in an additive or even synergistic effect. Without being bound to any theory, the reason for the additive or synergistic effect might be that each therapeutic mean has its own mechanism, and the combination of different mechanism results in an additive or synergistic effect.

Preferably, such further therapy includes, for example, the topical treatment with coal tar, dithranol, urea, salicylic acid and/or Mahonia aquifolium, the systemic treatment with fumaric acid, fumaric acid esters, and/or blockers of arachidonic acid, e.g. omega-3 fatty acids and/or the systemic or topical treatment with steroids, especially cortisone, vitamin D or derivatives thereof, vitamin A or derivatives thereof, vitamin B or derivatives thereof, especially vitamin B12, antibiotics, antimycotics, immunomodulators, e.g. methotrexate, cyclosporine, FK506, E-selectin blockers, P-selectin blockers, ICAM blockers, LFA-1 blockers, LFA-2 blockers, LFA-3 blockers, VCAM blockers, and/or TNF blockers, with cytokine inhibitors or T-cell activation inhibitors. The above blockers are e.g. antibodies or competitive inhibitors of E-selectin, P-selectin, ICAM, LFA-1, LFA-2, LFA-3, VCAM or TNF.

In the context of the present invention, the inhibitor may be administered as such, or preferably in combination with at least one excipient and/or auxiliary, e.g. with one or more suitable adjuvant(s) and/or one or more pharmaceutically active and/or acceptable carrier(s), diluent(s), filler(s), binder(s), disintegrant(s), lubricant(s), glident(s), coloring agent(s), flavoring agent(s), opaquing agent(s) and plasticizer(s).

Pharmaceutically acceptable salt forms of active compounds and standard pharmaceutical formulation techniques are well known to persons skilled in the art.

When the administration is topically, preferably said at least one excipient and/or auxiliary is hydrophobic and is preferably selected from the group comprising petroleum jelly, wax, oleyl alcohol, propylene glycol monostearate, propylene glycol monopalmitostearate, isopropyl laureate, isopropyl myristate, isopropyl palmitate, isopropyl stearate, ethyl myristate, propyl myristate, butyl myristate, ethyl oleate, cetylstearyl alcohol, Vaseline, lanolin alcohol or paraffin oil.

In a preferred embodiment of the present invention, at least two inhibitors are administered together. Particularly, effective combinations of fatty acid oxidation inhibitors can be the simultaneous use of a CPT-1 inhibitor and a FABP inhibitor, or the simultaneous use of a CPT-1 and CPT-2 inhibitor.

In a further aspect, the invention relates to the use of at least one inhibitor of fatty acid oxidation for the preparation of a pharmaceutical composition for the prophylaxis and/or treatment of a chronic and/or an atopic skin disease.

According to a preferred embodiment, the pharmaceutical composition prepared according to the use of the invention is intended to treat a human patient.

The inhibitor of the pharmaceutical composition prepared according to the use of the invention may be defined as above for the method of the invention.

Furthermore, the chronic or atopic skin disease may be defined as above for the method of the invention.

According to a preferred embodiment, the pharmaceutical composition prepared according to the use of the invention is for topic administration. The pharmaceutical compositions according to the invention for the topical route can be provided in the form of salves, creams, emulsions, milks, ointments, powders, impregnated pads, solutions, gels, sprays, lotions or suspensions. Moreover, the pharmaceutical compositions according to the invention can be provided in the form of shampoo, conditioner, hair tonic, hair spray, hair foam, hair paste or fixature. Same can also be provided in the form of lipid or polymeric microspheres or nanospheres or vesicles or of polymeric patches and hydrogels which permit controlled release. However, also the other routes of administration disclosed above for the method of the invention also apply here.

According to a further preferred embodiment, said pharmaceutical composition further comprises at least one additional active ingredient.

Preferably, said further active ingredient is selected from the group comprising coal tar, steroids, especially cortisone, vitamin D or derivatives thereof, vitamin A or derivatives thereof, vitamin B or derivatives thereof, especially vitamin B12, dithranol, urea, salicylic acid, Mahonia aquifolium, fumaric acid, fumaric acid esters, blockers of arachidonic acid, e.g. omega-3 fatty acids, antibiotics, antimycotics, immunomodulators, e.g. methotrexate, cyclosporine, FK506, E-selectin blockers, P-selectin blockers, ICAM blockers, LFA-1 blockers, LFA-2 blockers, LFA-3 blockers, VCAM blockers, and/or TNF blockers, with cytokine inhibitors and T-cell activation inhibitors. The above blockers are e.g. antibodies or competitive inhibitors of E-selectin, P-selectin, ICAM, LFA-1, LFA-2, LFA-3, VCAM or TNF.

According to a preferred embodiment, the pharmaceutical composition prepared according to the use of the invention comprises further auxiliaries and/or excipients as defined above.

Furthermore, all embodiments disclosed above for the method of the invention also apply to the use of the invention.

Because of possible additive or synergistic effects of several fatty acid oxidation inhibitors, the present invention further comprises the simultaneous use of two or more fatty acid oxidation inhibitors for the preparation of a pharmaceutical composition for the treatment of skin diseases. Particularly, effective combinations of fatty acid oxidation inhibitors can be the simultaneous use of a CPT-1 inhibitor and a FABP inhibitor, or the simultaneous use of a CPT-1 and CPT-2 inhibitor.

The invention further relates to a method for the production of a pharmaceutical composition for the prophylaxis and/or treatment of a chronic or an atopic skin disease, comprising the step of mixing at least one inhibitor of fatty acid oxidation with at least one excipient and/or auxiliary.

Preferably, the inhibitor is as defined above.

According to a preferred embodiment, said pharmaceutical composition is for topic administration.

According to a more preferred embodiment, the method comprises the further step of mixing the at least one inhibitor of fatty acid oxidation and the at least one excipient and/or auxiliary with at least one additional active ingredient. The active ingredient is preferably as defined above.

According to a preferred embodiment, said at least one excipient and/or auxiliary is preferably hydrophobic and is preferably selected from the group comprising petroleum jelly, wax, oleyl alcohol, propylene glycol monostearate, propylene glycol monopalmitostearate, isopropyl laureate, isopropyl myristate, isopropyl palmitate, isopropyl stearate, ethyl myristate, propyl myristate, butyl myristate, ethyl oleate, cetylstearyl alcohol, Vaseline, lanolin alcohol or paraffin oil.

All embodiments defined above for the use or method of the invention, as long as they apply to the inhibitor or to the pharmaceutical composition or to the administration thereof also apply to the method of the invention for the production of a pharmaceutical composition.

Furthermore, the invention relates to a method to investigate the effect of at least one fatty acid oxidation inhibitor on skin constitution in vitro, said method comprising the steps of cultivating cells under conditions essential for cell proliferation, adding of at least one fatty acid oxidation inhibitor to the cells, and monitoring the proliferation rate of the cells. Said cells are preferably keratinocytes or fibroblasts, especially human skin keratinocytes or skin fibroblasts.

Moreover, the invention relates to a method to investigate the effect of at least one fatty acid oxidation inhibitor on skin constitution in vivo, said method comprising the steps of topically administering at least one fatty acid oxidation inhibitor to the afflicted skin of an appropriate animal model, and monitoring the skin constitution. Appropriate animal models are selected from the group comprising the SCID mouse engrafted with human psoriatic skin, the BEIGE mouse, the NOA mouse, the NC/Nga mouse, the NC/Nga mouse treated with mite antigens, the fsn/fsn mouse, the IL-18 knock out mouse, the APO-C1 transgene mouse, the APO-C1 knock out mouse, the mouse tail test, the canine atopic dermatitis model, the transgenic mouse line expressing epidermal interleukin-4, the DNFB-induced allergic contact dermatitis in Gottingen minipigs, the hairless rat (WBN/Kob-Ht), the swine inflammation model induced by Phospholipase A2, and the basenji-greyhound (B-G) crossbreed dogs. An overview of psoriatic animal models is given in Schön 1999 (J Invest Dermatol 112(4):405-10). The skin condition or formation is monitored by visual inspection, optical coherence tomography (OCT), biopsy, microscopy or ultrasonic or infra-red measuring systems. Furthermore, immunological parameters, such as cytokine and/or T-cell activity and/or cell proliferation markers, such as Ki67, p34(cdc2), cyclin B1 or PCNA, can be measured.

The two methods of the invention for investigating the effect of at least one fatty acid oxidation inhibitor on skin constitution are especially applicable when the concentration and/or amount of the inhibitor in the pharmaceutical composition should be tested.

Furthermore, the present invention relates to a pharmaceutical composition for the prophylaxis and/or the treatment of chronic or atopic skin diseases comprising at least one inhibitor of fatty acid oxidation.

The agents inhibiting fatty acid oxidation are those which are described in more detail above. Said pharmaceutical composition may further comprise at least one excipient and/or auxiliary. In an especially preferred embodiment the pharmaceutical composition according to the present invention is intended to act topically. Such composition may further comprise at least one additional active ingredient, which is, for example, selected from the group comprising coal tar, steroids, especially cortisone, vitamin D or derivatives thereof, vitamin A or derivatives thereof, vitamin B or derivatives thereof, especially vitamin B12, dithranol, urea, salicylic acid, Mahonia aquifolium, fumaric acid, fumaric acid esters, blockers of arachidonic acid, e.g. omega-3 fatty acids, antibiotica, antimycotica, immunmodulators, e.g. methotrexate, cyclosporine, FK506, E-selectin blockers, P-selectin blockers, ICAM blockers, LFA-1 blockers, LFA-2 blockers, LFA-3 blockers, VCAM blockers, and/or TNF blockers, with cytokine inhibitors and T-cell activation inhibitors. The above blockers are e.g. antibodies or competitive inhibitors of E-selectin, P-selectin, ICAM, LFA-1, LFA-2, LFA-3, VCAM or TNF. The at least one excipient and/or auxiliary is preferably hydrophobic and is preferably selected from the group consisting of petroleum jelly, wax, oleyl alcohol, propylene glycol monostearate, propylene glycol monopalmitostearate, isopropyl laureate, isopropyl myristate, isopropyl palmitate, isopropyl stearate, ethyl myristate, propyl myristate, butyl myristate, ethyl oleate, cetylstearyl alcohol, Vaseline, lanolin alcohol or paraffin oil.

All embodiments defined above for the use or method of the invention, as long as they apply to the inhibitor or to the pharmaceutical composition or to the administration thereof also apply to the a pharmaceutical composition of the invention.

The present invention provides efficient pharmaceutical compositions and methods for the treatment of chronic and/or atopic skin diseases. Consequently, the present invention represents a veritable progress in that medical field.

Furthermore, the invention also relates to a method of preventing and/or treating leprosy by administering an inhibitor of fatty acid oxidation to a patient in a pharmacologically effective amount. With respect to the inhibitor, the excipients and auxiliaries, the administration of the inhibitor and the amount of inhibition to be administered, all embodiments disclosed above for the method of the invention to treat skin diseases also apply to the method of treating leprosy.

Leprosy (Hansen's Disease), sometimes called "Hanseniasis" or "H.D.", is a chronic mycobacterial disease, caused by Mycobacterium leprae, primarily affecting the peripheral nerves and secondarily involving skin and certain other tissues/organs, in particular the eye, mucosa of the nasal and upper respiratory tract and also the testes. Leprosy can be subdivided into two forms, lepromatous leprosy and tuberculoid leprosy.

It is known that in leprosy the fatty acid usage is enhanced due to the bacterial infection (Kato et al., 1993). Surprisingly, inhibiting the fatty acid oxidation according to the present invention elicits a positive effect on leprosy.

The invention further relates to the use of at least one inhibitor of fatty acid oxidation for the preparation of a pharmaceutical composition for the prophylaxis and/or treatment of leprosy. Also with respect to this aspect of the invention, all embodiments disclosed above for the use of the invention to prepare a pharmaceutical composition for the treatment of skin diseases also apply to the method of treating leprosy.

BRIEF DESCRIPTION OF THE FIGURES

FIG. 21 refers to the results of Example 2 and shows the afflicted skin areas 8 weeks after treatment; FIG. 21A depicts the Etomoxir-treated lesion, whereas FIG. 21B shows the placebo-treated lesion.

Figure 1:
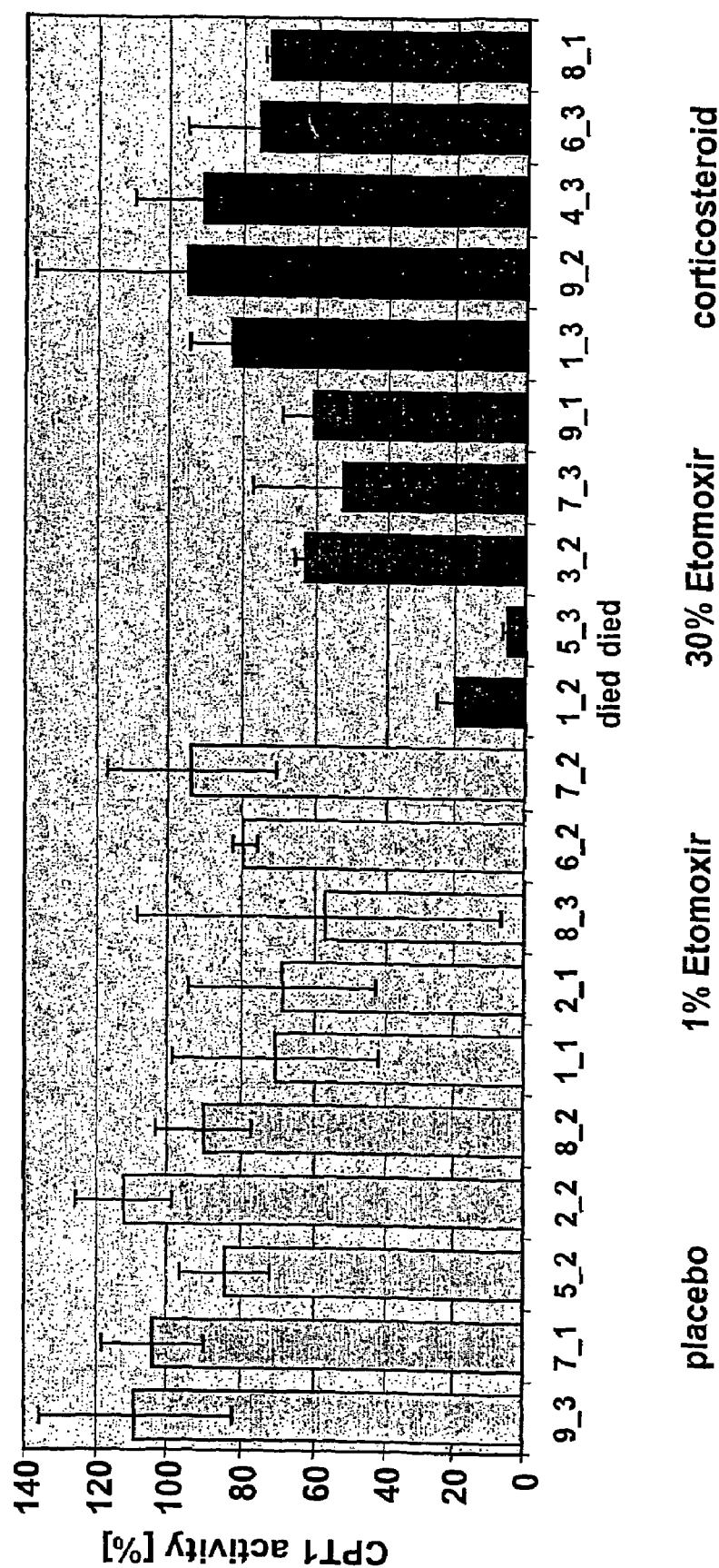
FIG. 1: CPT1 activity was determined in the liver of BNX mice after the three weeks treatment period. CPT 1 activities of two independent experiments were blotted in percentage compared to the placebo group, which was set 100%. Values from the mice which died shortly after the start of treatment are denoted. Standard deviations are depicted.

The following examples and figures are intended to illustrate the present invention without limiting the scope of the claims.

EXAMPLE 1

Abbreviations

| | |
|---|---|
| ATP | adenosine triphosphate |
| BSA | Bovine serum albumin |
| CoA | Coenzyme A |
| conc. | Concentration |
| cPI | complete, mini, EDTA-free Protease Inhibitor cocktail tablets |
| cpm | counts per minute |
| dd | Didestilled |
| ddH2O | double distilled water |
| DMSO | dimethylsulfoxide |
| DTT | DL-Dithiothreitol |
| EDTA | Ethylenediamine Tetraacetic acid |
| EGTA | Ethylene glycol-bis (β-amino ethyl ether)-N,N'-tetraacetic acid |
| GOT | Glutamat-Oxalacetat-Transaminase |
| GPT | Glutamat-Pyruvat-Transaminase |
| $H_2O$ | Water |
| $NH_4SO_4$ | Ammonium sulfat |
| OD | optical density |
| RT | Room temperatur |
| Tris | Tris(hydroxymethyl)aminomethane |
| w/o | without |

1. Methods

The following buffers have to be made with ddH$_2$O and cooled on ice prior to usage:

| Sucrose buffer Buffer No.: reagent/stock | Storage: RT amount | Shelf life: 1 year when filtered final conc. |
|---|---|---|
| 2 M Sucrose | 12.5 ml | 250 mM |
| 2 M Tris-HCl, pH 7.4 | 0.5 ml | 10 mM |
| 0.3 M EGTA; pH 7.4 | 33 µl | 0.1 mM |
| cPI (freshly added) | tablet/10 ml buffer | |
| ddH$_2$O | ad 100 ml | |

Remarks:
For storage buffer has to be filter sterilized.
cPI (complete, mini, EDTA-free Protease inhibitor cocktail tablets; Roche) containing aliquots have a shelf life of up to 2 weeks only.

| Buffer A Buffer No.: reagent/stock | Storage: RT amount | Shelf life: 1 year final conc. |
|---|---|---|
| 2 M KCl | 7.5 ml | 150 mM |
| 2 M Tris-HCl, pH 7.4 | 0.5 ml | 10 mM |
| cPI (freshly added) | 1 tablet/10 ml buffer | |
| ddH$_2$O | ad 100 ml | |

Remarks:
cPI containing aliquots have a shelf life of up to 2 weeks only.

| 4× Reaction buffer Buffer No.: reagent/stock | Storage: RT amount | Shelf life: 6 months final conc. |
|---|---|---|
| 2 M Sucrose | 22.0 ml | 880 mM |
| 2 M KCl | 5.0 ml | 200 mM |
| 2 M Tris-HCl, pH 7.4 | 1.0 ml | 40 mM |

-continued

| | | |
|---|---|---|
| 0.3 M EGTA, pH 7.4 | 0.66 ml | 4 mM |
| ddH$_2$O | ad 50 ml | |

| Reaction mix (n = 1) Buffer No.: reagent/stock | Storage: on ice amount | Shelf life: 1 day final conc. |
|---|---|---|
| 4× Reaction buffer | 50 µl | 2× |
| 5% fatty acid free BSA | 40 µl | 2% |
| 1 M DTT | 0.1 µl | 1 mM |
| 5 mM Palmitoyl-CoA | 4 µl | 0.2 mM |
| 50 mM L-carnitine | 2.4 µl | 1.2 mM |
| L-[methyl-$^3$H] Carnitine hydrochloride | 0.6 µl | |
| ddH$_2$O | 2.9 µl | |

Remarks:
At least a buffer volume of n + 4 has to be made; n = number of reactions

| 2× Activation mix (AM) (n = 1) Buffer No.: reagent/stock | Storage: on ice amount | Shelf life: 1 day final conc. |
|---|---|---|
| 2 M Tris-HCl, pH 7.4 | 5 µl | 200 mM |
| 2 M KCl | 2.5 µl | 100 mM |
| 0.1 M ATP | 6 µl | 12 mM |
| 1 mM CoA | 5 µl | 0.1 mM |
| 5% fatty acid free BSA | 6 µl | 0.6% |
| 1 M MgCl$_2$ | 0.65 µl | 13 mM |
| 0.1 M Glutathione | 0.35 µl | 0.7 mM |
| ddH$_2$O | 22.5 µl | |

Protocols

Animal Experiment:

The psoriasis model described by Wrone-Smith and Nickoloff (1996) was used. 5 mm non-lesional skin biopsies from five psoriatic patients were each split in four pieces and transplanted on 20 immuno-deficient BNX mice, i.e. four groups of five mice each. Psoriasis was induced in all mice by injection with donors super-antigen-activated blood cells. After psoriasis had developed, mice were treated for 3 weeks by applying either placebo-cream, cream containing a corticosteroid (betamethasone), 1% Etomoxir or 30% Etomoxir daily on the skin. The cream containing 30% Etomoxir was removed after 30 minutes while the other creams were left on the skin. The reason for the different treatment of the 30% Etomoxir group was, that two out of five animals died shortly after the treatment probably because they licked off the cream.

After the treatment period, liver and blood of the mice were analyzed for their CPT1 activity and GOT/GPT levels. Furthermore, the epidermal thickness, in particular the depth of reti ridges, the number of Ki67 positive cells and the percentage of ULEX-positive cells (this marker stains the the upper layers of the epidermis in normal skin and the whole epidermis in psoriatic skin) in the epidermis were determined.

Preparation of Mitochondrial Enriched Fractions from Liver Samples:

A small piece of frozen liver (appr. 200 mg) was homogenized in 600 µl of cold sucrose buffer by 8-10 strokes with tight pestle of dounce homogenizer. Homogenate was centrifuged at 700×g for 10 min at 4° C. Supernatant was again centrifuged at 20000×g for 20 min at 4° C. Pellet was resuspended in 1400 µl buffer A and kept on ice for further analysis or stored at −80° C.

Preparation of Total Blood Cell Extract:

500 µl of total blood cells were frozen and drawn three tines to break up the cells. Samples were diluted by adding 500 µl buffer A and then centrifuged at 20000×g for 20 min at 4° C. Solid Pellets were resuspended in 200 µl buffer A and kept on ice for further analysis or stored at −80° C.

Determination of Protein Concentration with the Bradford Assay:

160 µl of bidestilled water was added to wells of a 96-well plate. For the standard curve 0 µg, 1 µg, 2 µg, 3 µg, 4 µg and 5 µg of BSA (BSA stock: 1 mg/ml from New England Biolabs) was added in duplicates to the first 10 wells. 1 µl of the liver samples and the blood samples were added in duplicates to the wells. Finally 40 µl dye reagent concentrate (Bio-Rad protein assay) was added and mixed by pipetting up and down. After 5 to 30 min OD at 595 was measured versus reagent blank (0 µg BSA). For the calibration curve the OD was plotted against the concentration of BSA and total protein concentration of the liver samples was calculated in µg/µl.

Determination of CPT1 Activity In Vitro:

20 µg of total protein of each liver sample and 300 µg of total protein of each plasma sample were added in 1.5 ml Eppendorf tubes (safe lock) and filled up to 100 µl with buffer A (all in duplicates). Background control was buffer A only. The tubes were preincubated for exactly 5 min at 30° C. prior to the addition of 105 µl of reaction mix. Again samples were incubated for exactly 5 min at 30° C. Reactions were stopped by adding 800 µl of 6% perchloric acid and stored on ice. Tubes were vortexed briefly and then centrifuged at 4000 rpm for 5 min. Supernatant was removed and pellets were washed by rinsing with 750 µl of 6% perchloric acid. After another centrifugation step at 4000 rpm for 2 min supernatant was completely removed. Pellet was dissolved as good as possible in 600 µl of bidestilled water by strongly shaking for at least 15 min. 400 µl of butanol, 150 µl of 6% perchloric acid and 150 µl of saturated ammonium sulfate were added one after the other and tubes were briefly vortexed after each addition. Tubes were vortexed for further 10 min. Finally, either 100 µl (liver samples) or 150 µl (plasma samples) of the butanol phase were mixed with 1 ml Microscint0 in a 24 well-plate and cpm values were measured with the scintillation counter from Canberra Packard.

Inhibition of CPT1 Activity by the Salt of Etomoxir In Vitro:

2 µl of a 100× stock of Etomoxir-salt (0; 0.1; 1.0 and 10 mM) dissolved in DMSO were added in 1.5 ml Eppendorf tubes in duplicates. 2× activation mix was premixed on ice with either 15 µg of total protein of each liver sample or 300 µg of total protein of each plasma sample (final volume per reaction was 98 µl). 98 µl of this mix was added to each tube containing the 2 µl of inhibitor and tubes were left at 30° C. for exactly 30 min. Then 105 µl of reaction mix were added to start the CPT1 reaction. Again samples were incubated for exactly 5 min at 30° C. Reactions were stopped by adding 800 µl of 6% perchloric acid and stored on ice. Tubes were vortexed briefly and then centrifuged at 4000 rpm for 5 min. Supernatant was removed and pellets were washed by rinsing with 750 µl of 6% perchloric acid. After another centrifugation step at 4000 rpm for 2 min supernatant was completely removed. Pellet was dissolved as good as possible in 600 µl of bidestilled water by strongly shaking for at least 15 min. 400 µl of butanol, 150 µl of 6% perchloric acid and 150 µl of saturated ammonium sulfate were added one after the other and tubes were briefly vortexed after each addition. Tubes were vortexed for further 10 min. Finally, either 150 µl of the butanol phase were mixed with 1 ml Microscint0 in a 24 well-plate and cpm values were measured with the scintillation counter from Canberra Packard. P values were calculated with the t-test of the SigmaPlot 2001 software.

Preparation of Total Protein Containing Homogenate from Mouse Skin

A mouse was shaved before skin was taken off. A small piece of frozen skin (Ø 5-10 mm) was cut in smallest pieces with scissors and put in a 2 ml tube with appr. 1 ml cold sucrose buffer. Skin pieces were homogenized with a hand mixer (IKA Ultra Turrax T8) on ice. Homogenate was pounded appr. 6 times with tight pestle of homogenizer. Homogenate was centrifuged at 21000×g for 20 min at 4° C. Pellet was resuspended in 200 µl buffer A. Either the final mouse skin sample was kept on ice for further analysis or stored in 50 µl aliquots at −80° C.

Preparation of Total Protein Containing Homogenate from Human Skin

A small piece of frozen skin (Ø 5 mm or 50 mg) was cut in smallest pieces with scissors and put in a 2 ml tube with appr. 1 ml cold sucrose buffer. Skin pieces were homogenized as good as possible with a hand mixer (IKA Ultra Turrax T8) on ice. Homogenate was pounded appr. 6 times with tight pestle of homogenizer. Pestle did not reach the bottom of the tube because of some larger skin pieces which could not be homogenized completely. Homogenate was centrifuged at 21000×g for 20 min at 4° C. Pellet was resuspended in 200 µl buffer A. Either the final mouse skin sample was kept on ice for further analysis or stored in 50 µl aliquots at −80° C.

Determination of Protein Concentration with the Bradford Reagents:

160 µl of ddH$_2$O was added to each well of a 96-well plate. For the standard curve 0 µg, 1 µg, 2 µg, 3 µg, 4 µg and 5 µg of BSA (BSA stock: 1 mg/ml from New England Biolabs; 1/10 diluted) was added in duplicates to the first 10 wells. 1 µl and 3 µl of the mouse skin samples were added in duplicates to the wells. Finally 40 µl Bradford reagent was added with the multipette and mixed by pipetting up and down. After 5 to 30 min OD at 595 was measured in the Elisa reader versus reagent blank (0 µg BSA). For the calibration curve the OD was plotted against the concentration of BSA and total protein concentration of the samples was calculated in µg of total protein/µl.

Determination of CPT1 Activity In Vitro:

To determine the amount of total protein needed to get an CPT1 activity of appr. 300 cpms samples with increasing amounts of total protein (0-100 µg) were measured for their CPT1 activity. Mouse and human skin samples were put in 1.5 ml Eppendorf tubes (safe lock) and filled up to 100 µl with buffer A (all in duplicates). As a background control only 100 µl of buffer A is put in two tubes. The tubes were preincubated for exactly 5 min at 30° C. Then 100 µl of reaction mix were added and samples were again incubated for exactly 5 min at 30° C. Reactions were stopped by adding 800 µl of 6% perchloric acid and tubes were stored on ice until all reactions had been finished. Tubes were vortexed briefly and then centrifuged at 4000 rpm for 5 min. All the remaining steps were performed at RT. Supernatants were removed and pellets were washed by adding 750 µl of 6% perchloric acid (multipette) and upturning tubes 3 times. After another centrifugation step at 4000 rpm for 2 min supernatants were completely removed by quickly removing the major part of each supernatant then briefly spinning and removing the remaining of the supernatant with a 200 µl pipette. Pellets were dissolved (sometimes a small pellet is left) in 600 µl of ddH$_2$O (multipette) by shaking on the VIBRAX shaker for 15 min at maximal speed. Working under the hood, 400 µl of water-saturated butanol, 150 µl of 6% perchloric acid and 150 µl of saturated ammonium sulfate were added one after the other with the multipette and tubes were vortexed for 3 min on the VIBRAX shaker (maximal speed) after each addition. Tubes were vortexed for further 10 min on the VIBRAX shaker (maximal speed). Finally, 100 µl of the upper butanol phase were mixed with 1 ml Microscint0 in a 24 well-plate and cpm values were measured with the scintillation counter from Canberra Packard using the settings recommended by the manufacturer for tritium measurements.

Inhibition of CPT1 Activity by the Salt of Etomoxir In Vitro:

2 µl of a 100× stock of Etomoxir-salt (0; 0.1; 1.0 and 10 mM) dissolved in DMSO were added in 1.5 ml Eppendorf tubes in duplicates. 48 µl of 2× activation mix was premixed on ice with 50 µl of skin samples containing a fixed amount of total protein with which CPT1 activity reaches appr. 300 cpm (e.g. for human skin this was appr. 50 mg of total protein; volume was filled up to 50 µl with buffer A). The final volume per reaction was 98 µl. A premix of n+4 (n=number of reactions) was made. 98 µl of this premix was added to each tube containing the 2 µl of inhibitor and tubes were left at 30° C. for exactly 30 min. Then 100 µl of reaction mix were added to start the CPT1 reaction. Again samples were incubated for exactly 5 min at 30° C. Reactions were stopped by adding 800 µl of 6% perchloric acid and stored on ice. Tubes were vortexed briefly and then centrifuged at 4000 rpm for 5 min. Supernatant was removed and pellets were washed by rinsing with 750 µl of 6% perchloric acid. After another centrifugation step at 4000 rpm for 2 min supernatant was completely removed. Pellet was dissolved as good as possible in 600 µl of bidistilled water by strongly shaking for at least 15 min. 400 µl of butanol, 150 µl of 6% perchloric acid and 150 µl of saturated ammonium sulfate were added one after the other and tubes were briefly vortexed after each addition. Tubes were vortexed for further 10 min. Finally, 100 µl of the butanol phase were mixed with 1 ml Microscint0 in a 24 well-plate and cpm values were measured with the scintillation counter as described above.

Figure 20:
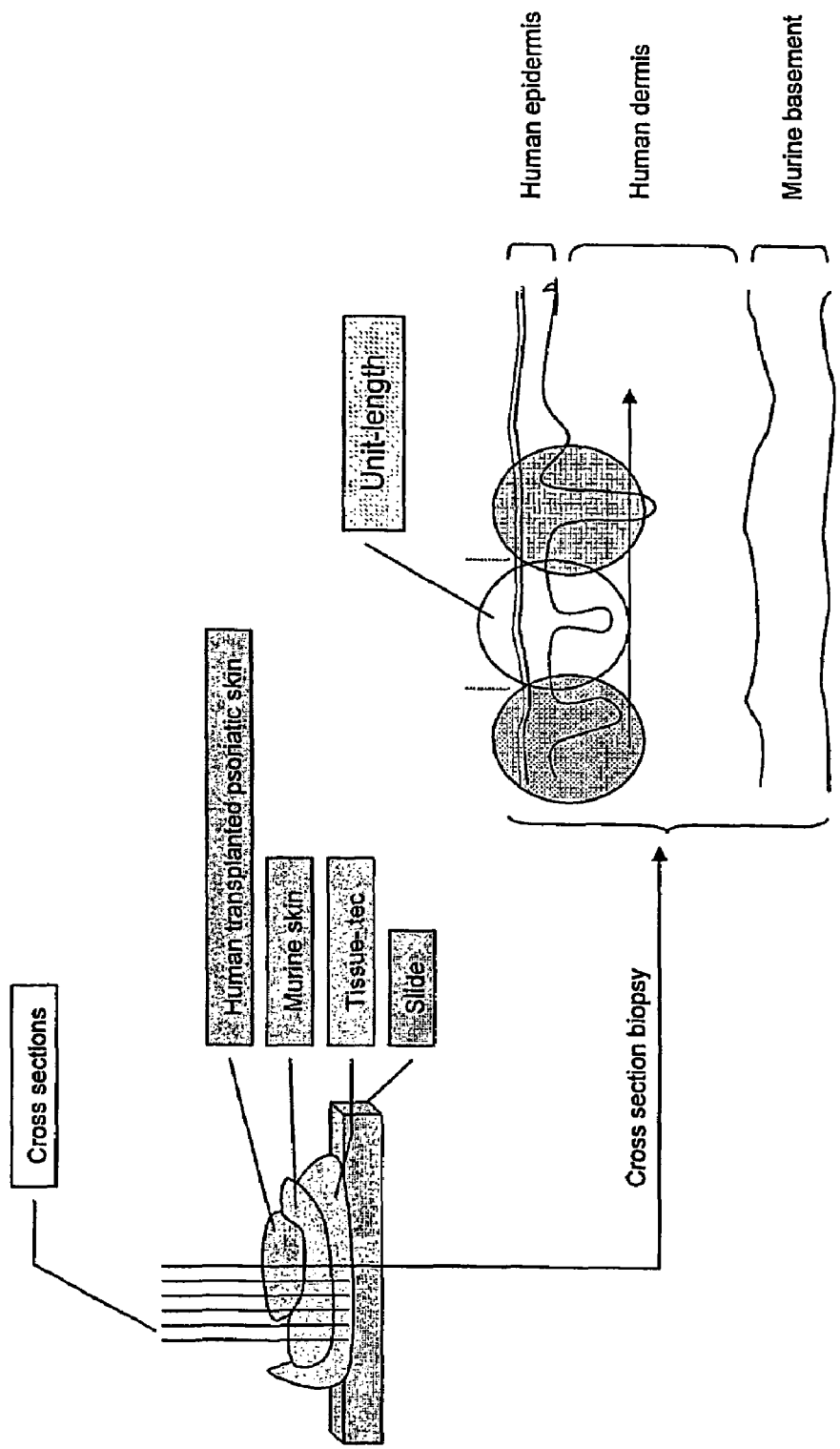
FIG. 20: Schematic representation of human skin transplanted on BNX-mice.

Determination of Epidermal Thickness, the Number of Ki67 Positive Cells and the Percentage of ULEX-positive Cells:

Histological stainings are performed on cryo-preserved tissues. Diagonal cross sections (8µm) are cut (see FIG. 20), covering all skin-layers (located at the top layer are the stratum corneus and epidermis of the transplanted human biopsy and at the bottom the murine tissue is located, forming a base for the transplanted human skin).

1. Hematoxyline Staining (Epidermal Thickness)

Sections are stained with hematoxyline and evaluated at a microscopic magnification of 200×. Two sections taken round the middle of the biopsy are evaluated. Thickness measurements are performed of the total section using a microscopic ocular with intergraded graduation-lines (ruler). From this, the average epidermal thickness measurements for ridges and the average of the total epidermis (mean of ridges and inter-ridges) are calculated in µm (taken into account magnification factor).

2. Ki-67 Staining (Keratinocyte Proliferation)

Sections are stained with mu-∝Hu monoclonal Ab and evaluated at a microscopic magnification of 400×. Two representative sections are evaluated. The total number of positive cells are counted of the total section and indicated per unit-length. A unit-length is a microscopic view (of a part of the section) at a magnification of 400× (see FIG. 20). Per section several unit-lengths are counted (minimum of 8). From this the average number of Ki-67 positive cells per unit-length is calculated.

3. ULEX Staining (Keratinocyte Differentiation)

Sections are stained with biotinylated Europaeus Agglutinin 1 and evaluated at a microscopic magnification of 200×. Two representative sections are evaluated. The thickness of both the ULEX positive cell-layer (distribution of ULEX) as well as the ULEX negative layer of the total section is measured using a microscopic ocular with intergraded graduation-lines (ruler). From this the average ratio of ULEX positive differentiation is calculated (indicated as percentage of epidermis positive for ULUX).

2. Results

Biochemical Analysis of the Liver

Figure 2:
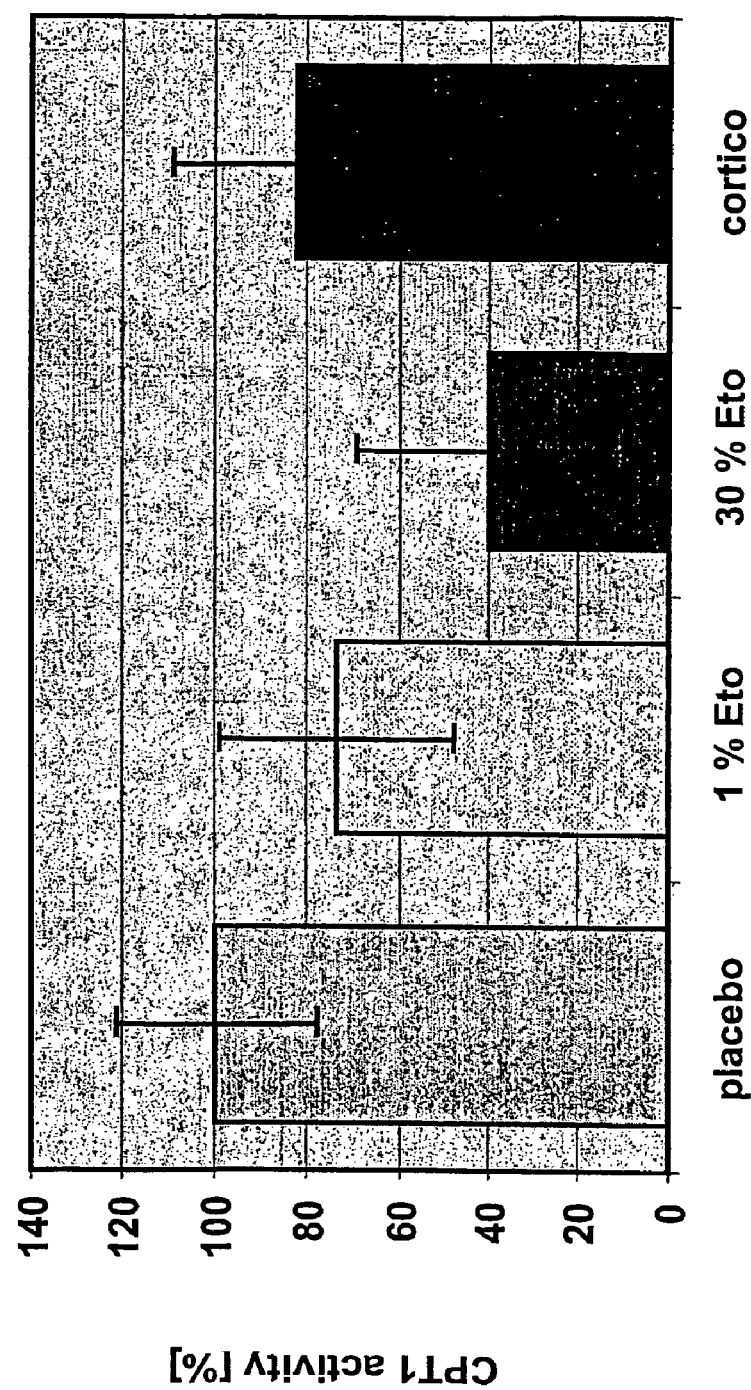
FIG. 2: Summary of FIG. 1. CPT 1 activity was determined in liver of BNX mice. Each group consists of 5 animals. The two dead animals of the 30% Etomoxir group were included. Standard deviations are depicted.
Figure 3:
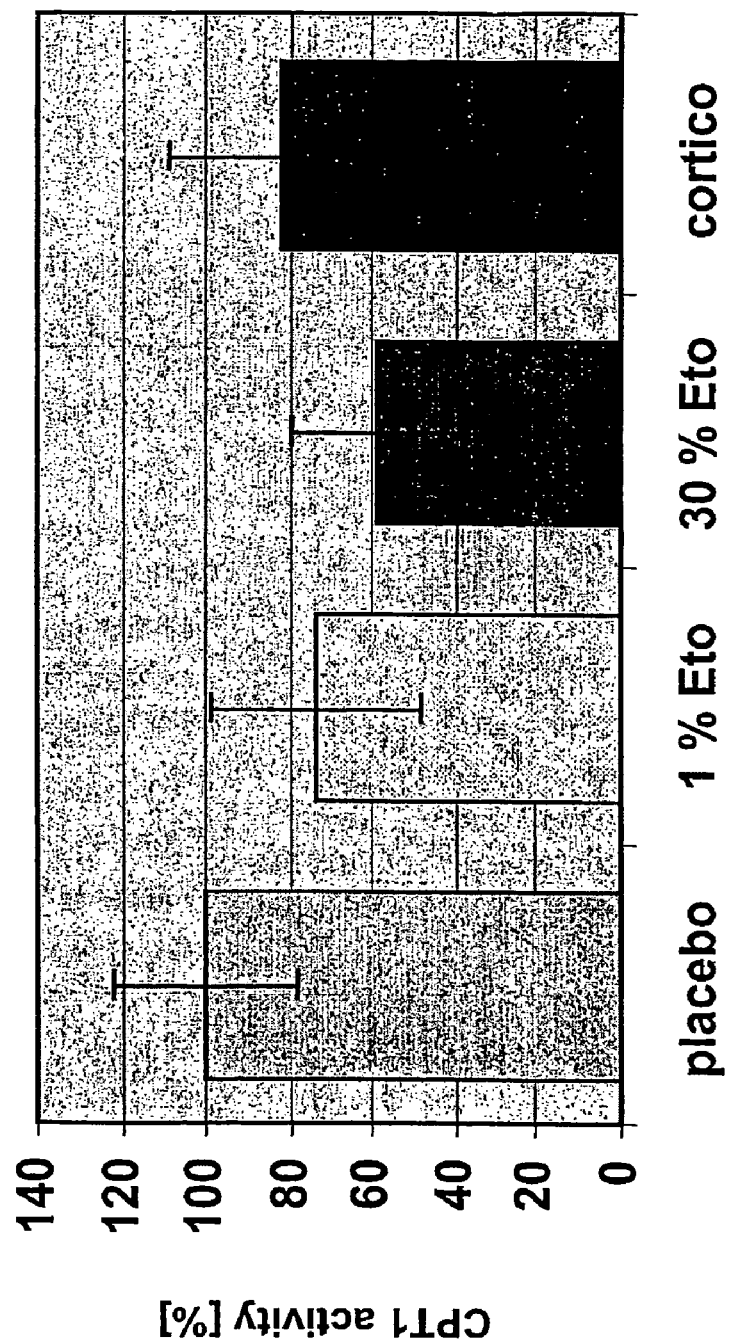
FIG. 3: Summary of FIG. 1. CPT1 activity was determined in liver of BNX mice. The placebo, the 1% Etomoxir and the corticosteroid group consisted of 5 animals. The 30% Etomoxir group consisted of 3 animals because the two dead animals were excluded. Standard deviations are depicted.

After the treatment period BNX mice were sacrificed and the liver was removed and stored at −80° C. for further analysis. CPT1 assays with liver samples were carried out as described in the methods. The whole procedure was repeated once. In FIG. 1 the percentage of mean CPT1 activities of all animals of the two independent experiments are shown. The placebo group was set as 100%. FIGS. 2 and 3 are summaries of FIG. 1, which either include or exclude the two dead animals in the 30% group.

The experiment showed that the corticosteroid group has a slightly reduced CPT1 activity (83%) compared to the placebo group (FIGS. 1 and 2). However, this difference was not statistically significant (p=5.64E-02). The CPT1 activity of the 1% Etomoxir group was 73%. This difference was statistically significant (p=1.56E-02), when compared to the control group and very similar to the corticosteroid group. The strongest decrease in CPT1 activity (40% and 59% excluding liver of dead animals) was detected in the 30% Etomoxir group (FIGS. 2 and 3). These differences are highly significant with p values of 9.54E-06 (including dead animals) and 1.38E-04 (excluding dead animals).

In summary, this small animal experiment, in which licking was not avoided, the 1% Etomoxir group seems still to have acceptable CPT1 activity levels which were comparable to the control group. However, the 30% Etomoxir group has significantly lower levels. From this experiment it could not be ruled out if the strongly reduced levels in the 30% Etomoxir group and the slightly but significantly reduced levels in the 1% Etomoxir group were due to licking and not a result of penetration of Etomoxir through the skin.

Biochemical Analysis of Total Blood Cells

Figure 4:
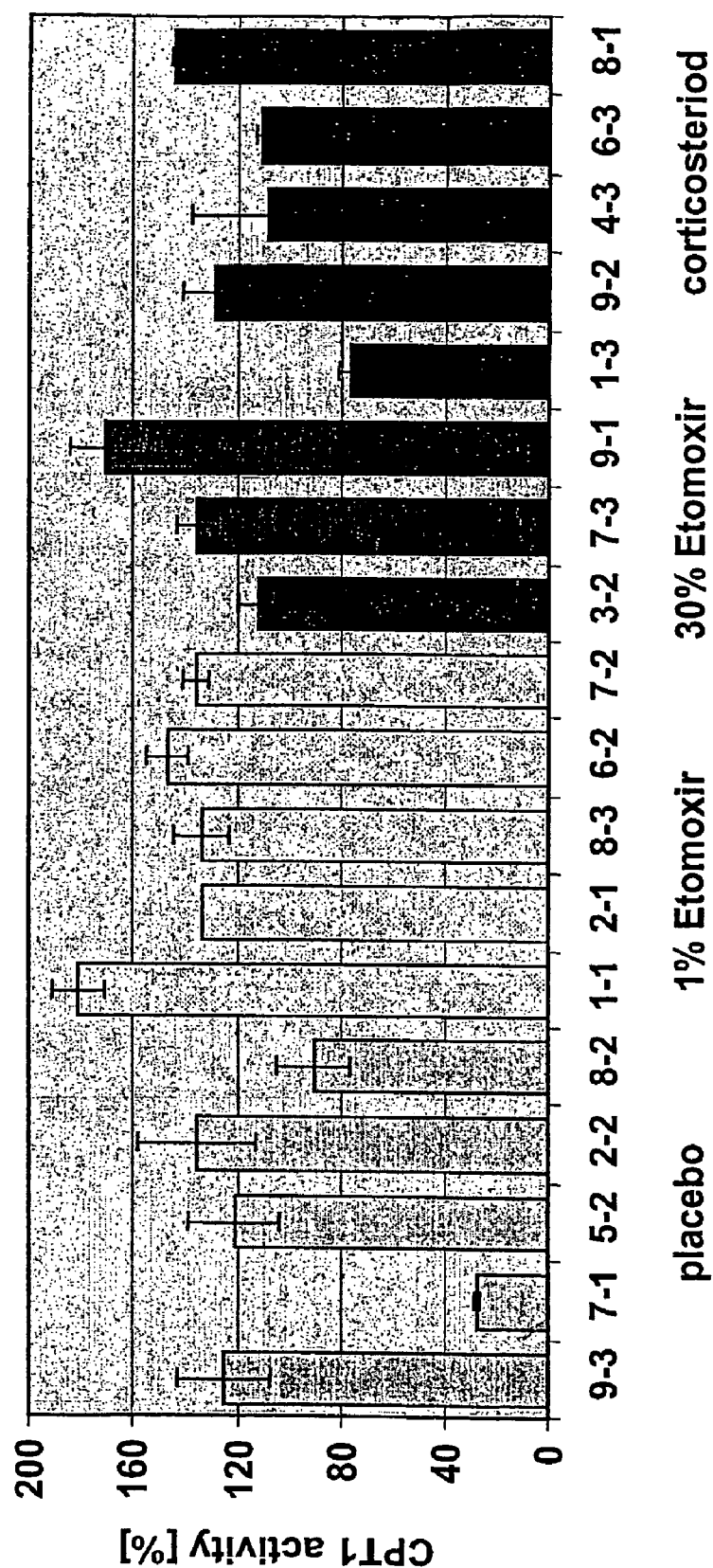
FIG. 4: CPT 1 activity was measured in blood cells of BNX mice after the three weeks treatment period. CPT 1 activities of two independent experiments were blotted in percentage compared to the placebo group, which was set 100%. Standard deviations are depicted.
Figure 5:
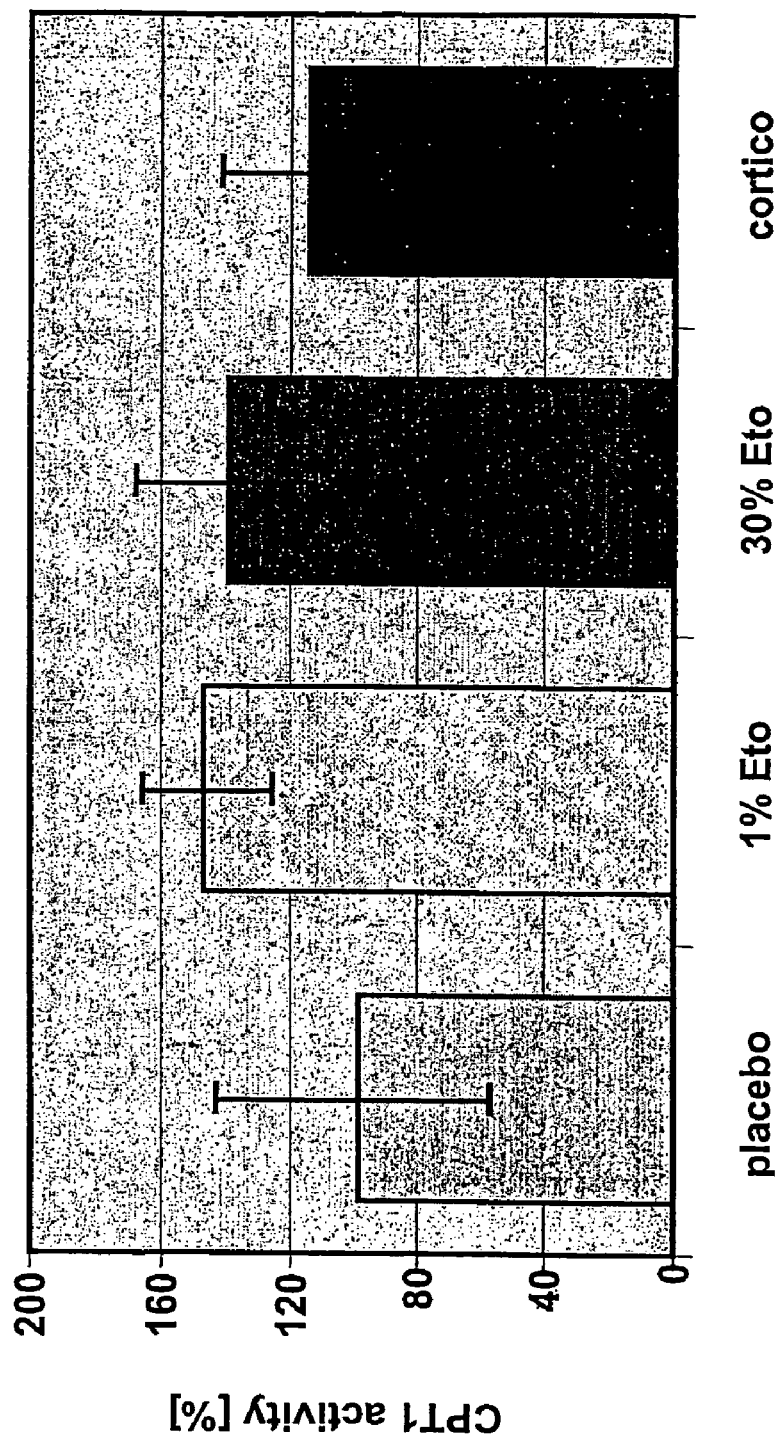
FIG. 5: Summary of FIG. 4. CPT1 activity was measured in blood cells of BNX mice. The placebo, the 1% Etomoxir and the corticosteroid group consisted of 5 animals. The 30% Etomoxir group consisted of 3 animals because the two dead animals were excluded. Standard deviations are depicted.

After the treatment period the blood was collected and citrate was added to prevent blood clotting. The blood was centrifuged for 10 min at 1200 rpm. The plasma and the cell pellet were separated and stored at −80° C. for further analysis. CPT1 assays with the cell pellets were carried out as described in the methods. The whole procedure was repeated once. In FIG. 4 the mean CPT1 activities of the two independent experiments of all individual samples were blotted. The placebo was set to 100%. FIG. 5 is a summary of FIG. 4. The blood of the two animals which died in the 30% Etomoxir group was not collected.

CPT1 activities derived from the cell pellets were not significantly different in animals of the placebo group, the 30% Etomoxir group and the corticosteroid group (p value>0.05). Only the CPT1 activities in the 1% Etomoxir group were significantly higher than in the placebo group (p value 0.01).

Figure 6:
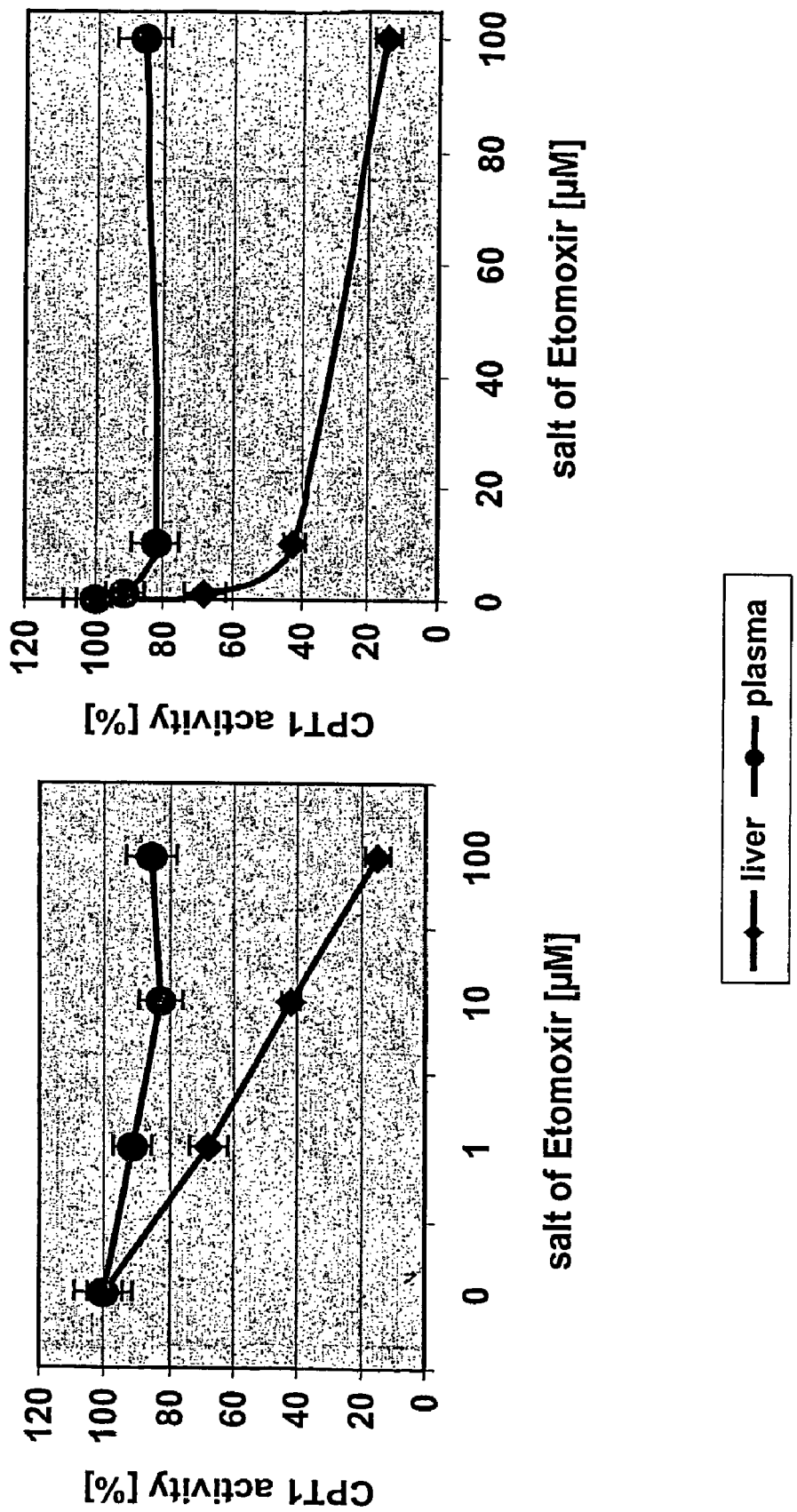
FIG. 6: Treatment of blood cells and mitochondrial enriched fractions of liver samples with increasing concentrations of the salt of Etomoxir prior to the measurement of the CPT1 activity. CPT1 activity achieved without Etomoxir was set to 100%. Standard deviations are depicted.

To determine the sensitivity of the CPT1 activity in response to Etomoxir, cell pellet samples were pooled and treated with increasing amounts of Etomoxir. CPT1 activity was only reduced appr. by 15% (FIG. 6). In contrast CPT1 activities measured in liver were highly Etomoxir sensitive. This means that appr. 85% of the measured activity in the blood cells was Etomoxir insensitive and therefore the relevance of this assay is questionable.

GPT/GOT Levels in the Blood Plasma

Figure 7:
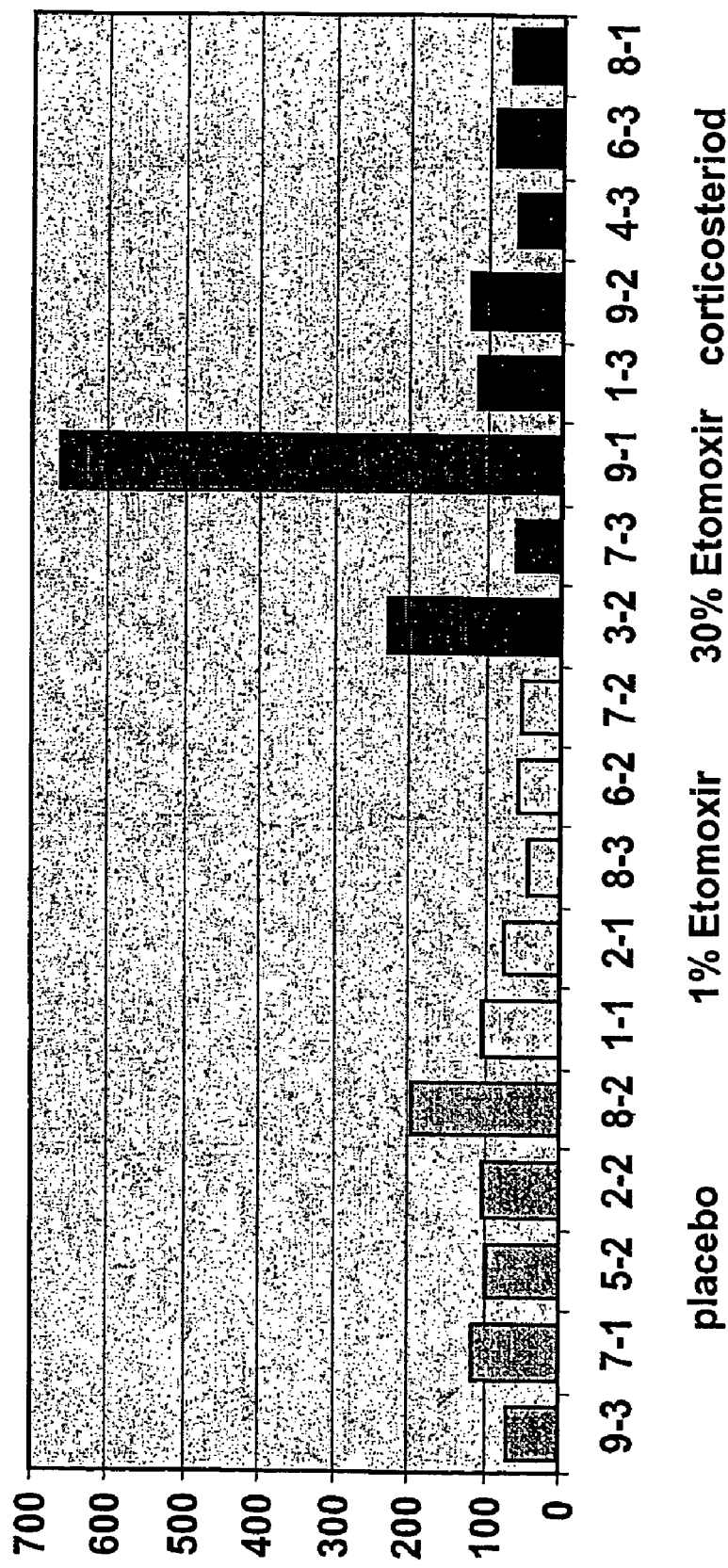
FIG. 7: GPT levels in each plasma sample of the BNX mice.
Figure 8:
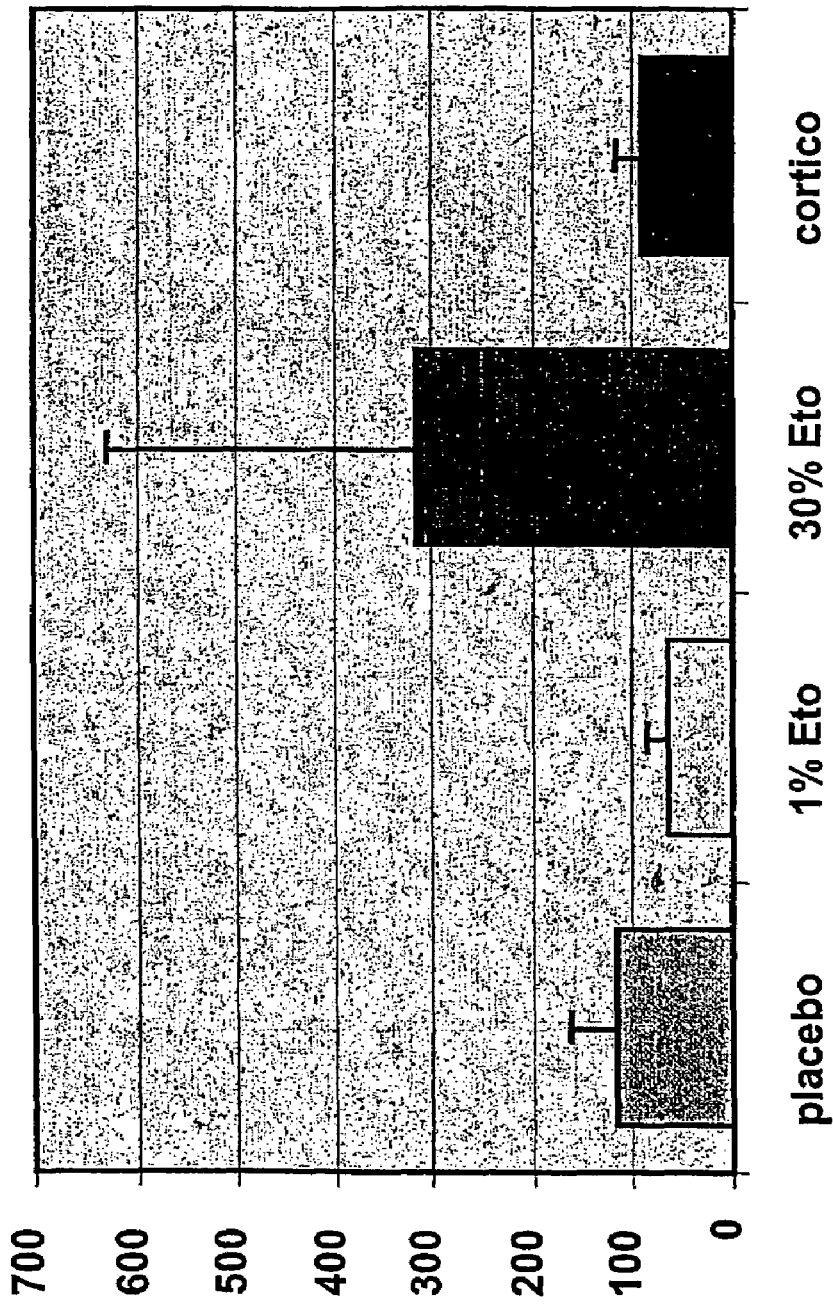
FIG. 8: Summary of FIG. 7. GPT levels in BNX mice. Standard deviations are depicted.
Figure 9:
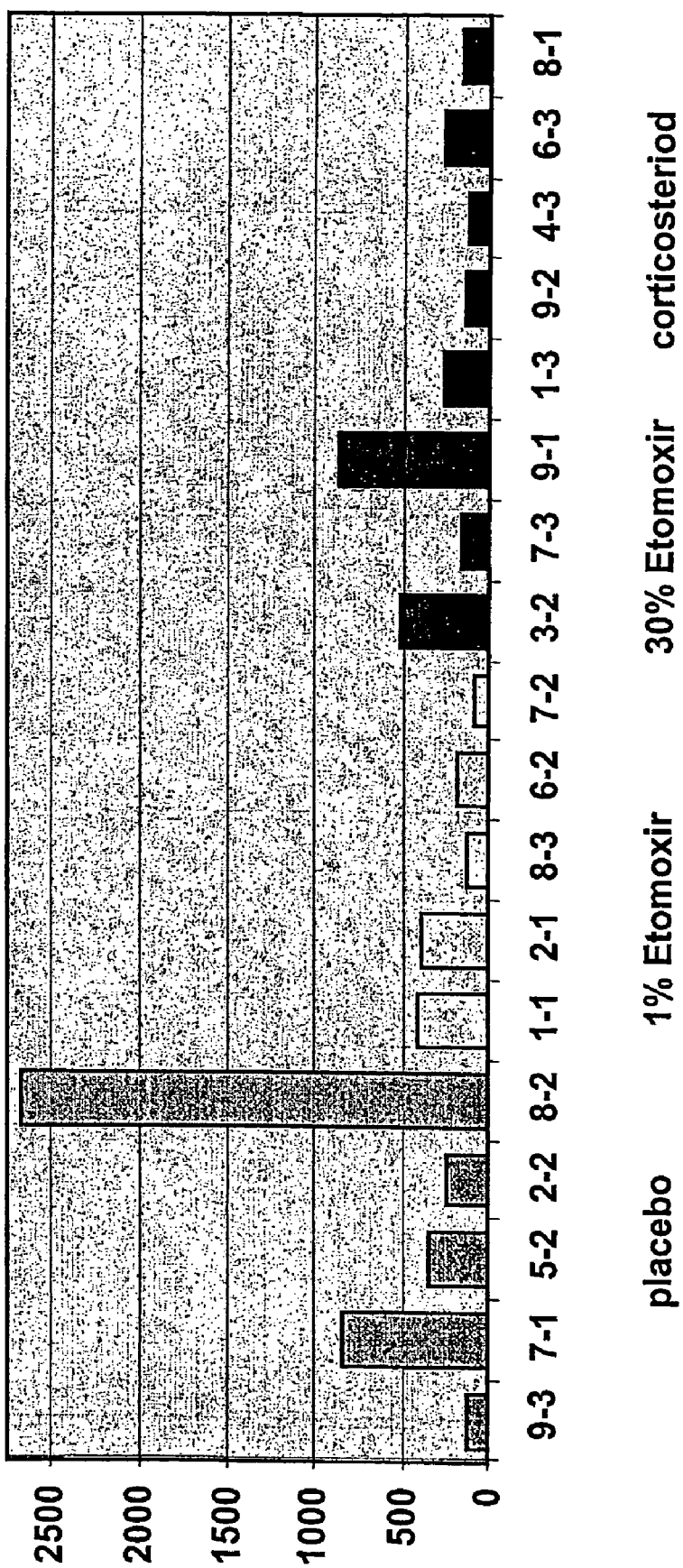
FIG. 9: GOT levels in each plasma sample of the BNX mice.
Figure 10:
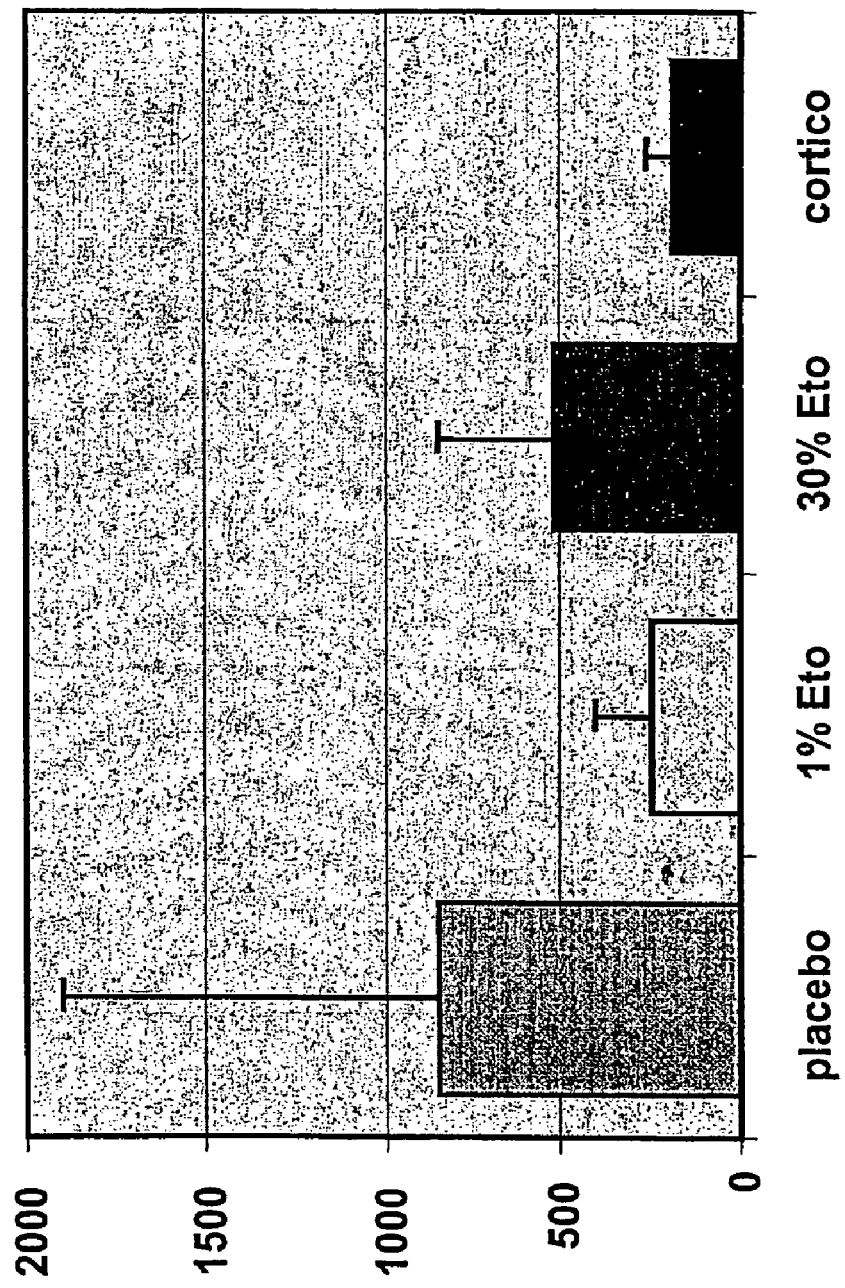
FIG. 10: Summary of FIG. 9. GOT levels in BNX mice. Standard deviations are depicted.

GPT and GOT levels were measured by Med-Lab GmbH (Munich) in the plasma samples derived from the BNX mice which were stored at −80° C. The liver specific GPT levels were only increased in the 30% Etomoxir group (FIG. 7). The GOT level, which is a marker for liver, heart and skeletal muscle, was also increased in two out of three mice of the 30% Etomoxir group and in one placebo mouse (FIG. 9). The reason for the increased GOT level in the placebo mouse is unknown. In summary, increased GOT and GPT levels were only detected in the high dosage Etomoxir group (FIGS. 8 and 10). However, the difference was not statistically significant (p>0.05; the number of animals in the 30% Etomoxir group was probably too low). It has to be Figured out whether the increased levels of liver enzymes in the 30% Etomoxir group were due to penetration of Etomoxir through the skin or due to licking.

Biochemical Analysis of the Skin

Figure 11:
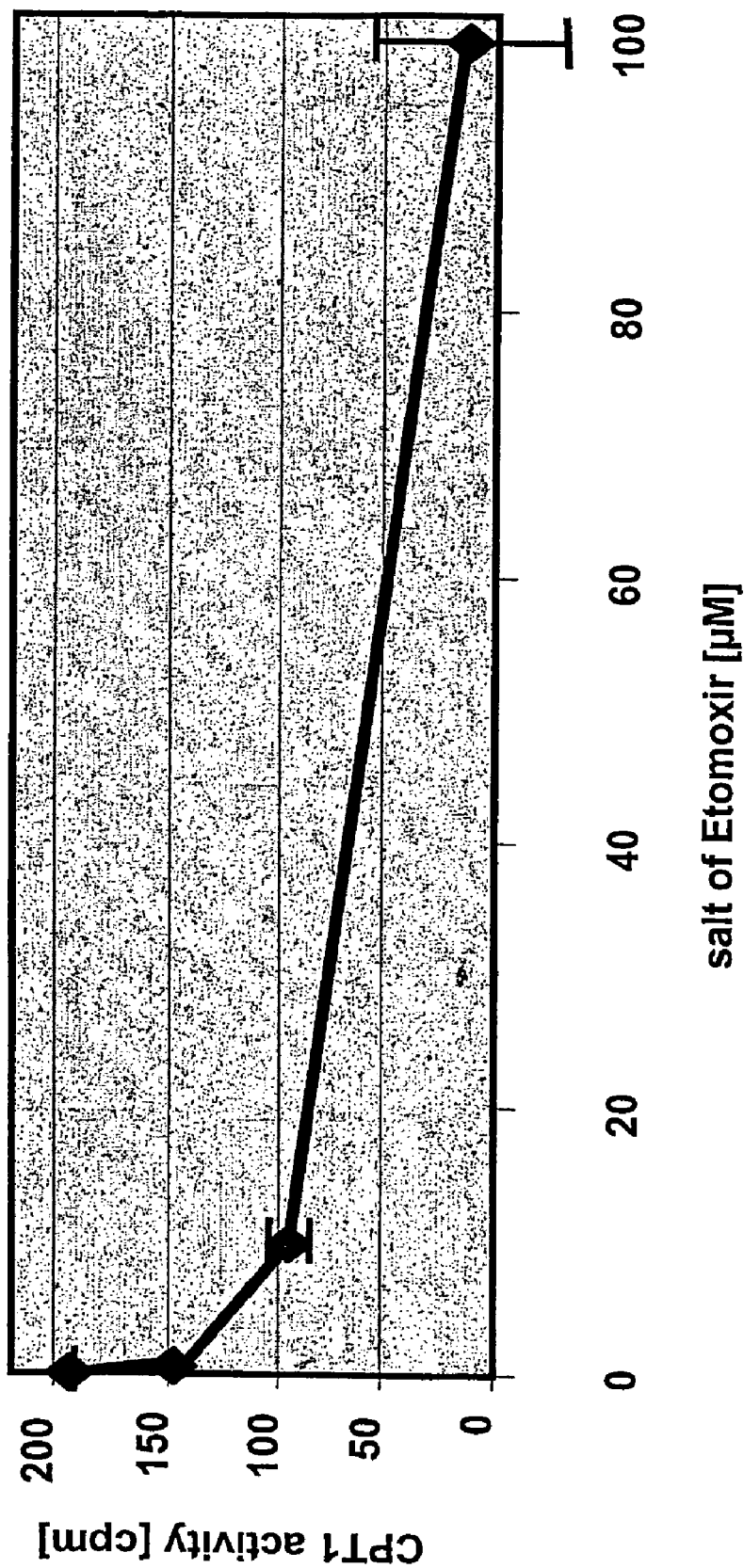
FIG. 11: Treatment of total skin extract with the salt of Etomoxir prior to the measurement of the CPT1 activity. Skin samples were derived from healthy mouse skin. CPT1 activity is blotted in activity in cpm against the amount of Etomoxir in the samples.
Figure 12:
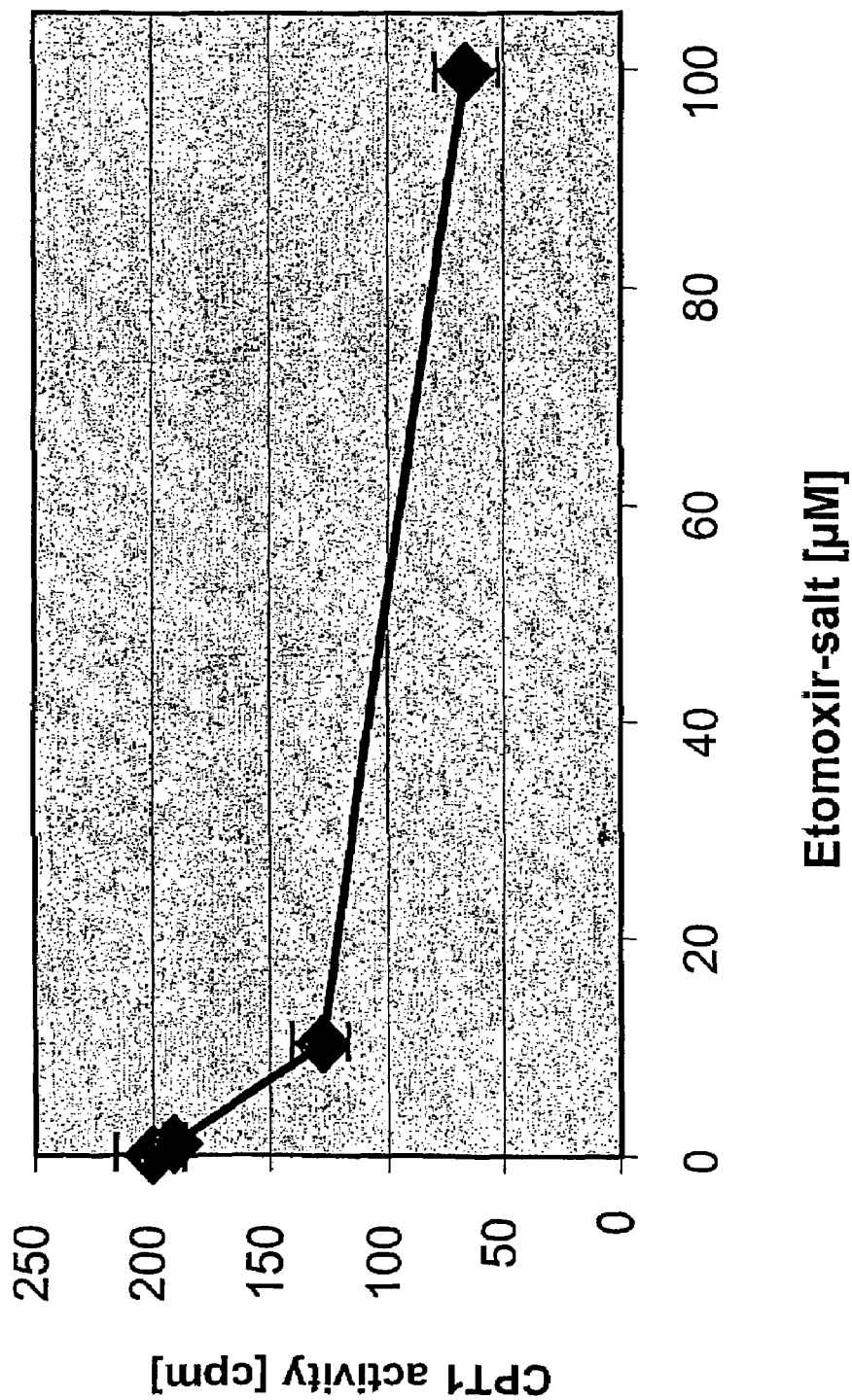
FIG. 12: Treatment of total skin extract with the salt of Etomoxir prior to the measurement of the CPT1 activity. Skin samples were derived from healthy skin from a human skin cancer patient. CPT1 activity is blotted in activity in cpm against the amount of Etomoxir in the samples.
Figure 13:
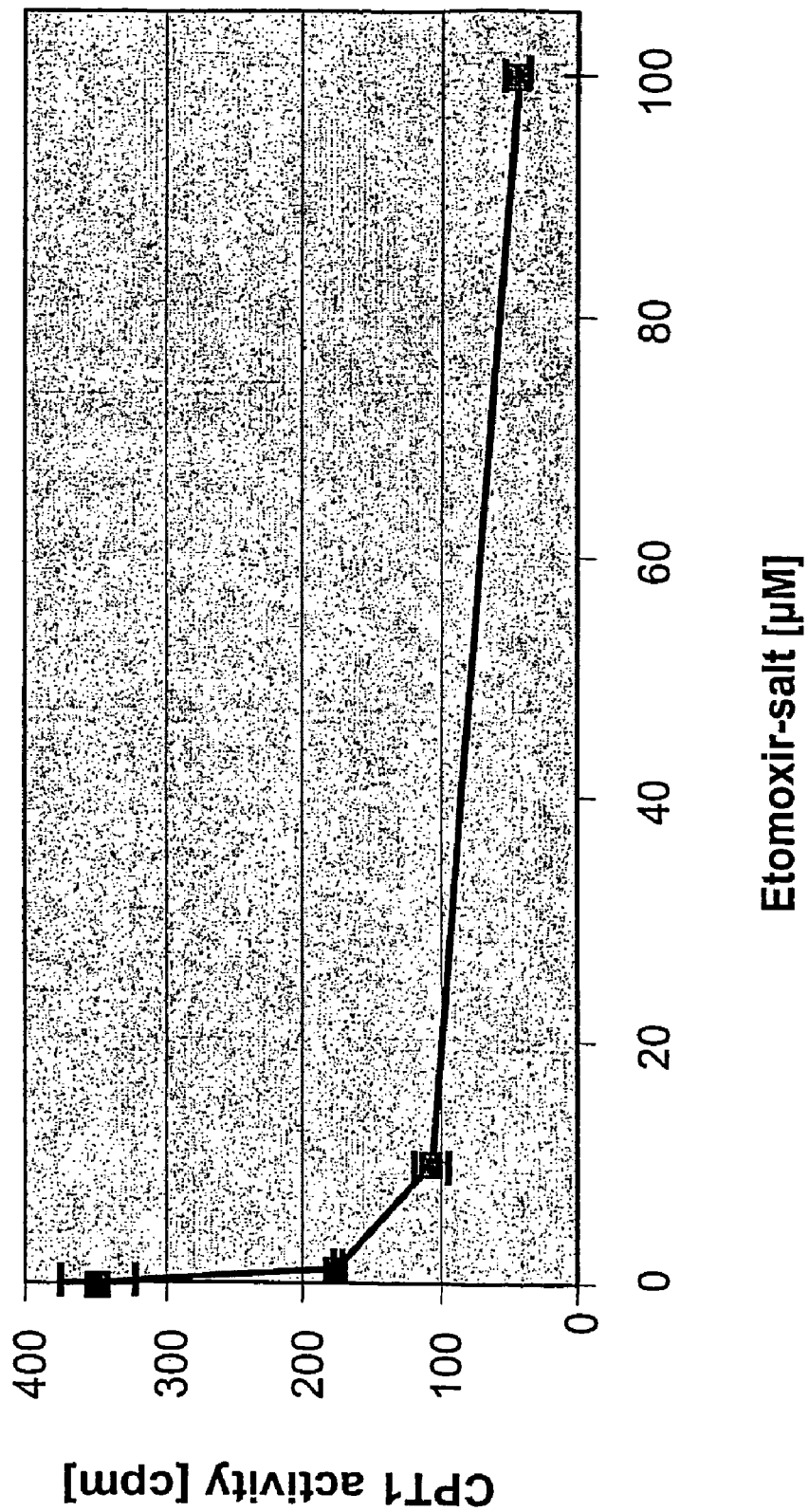
FIG. 13: Treatment of total skin extract with the salt of Etomoxir prior to the measurement of the CPT1 activity. Skin samples were derived from psoriatic skin from a human psoriasis patient. CPT1 activity is blotted in activity in cpm against the amount of Etomoxir in the samples.

Treatment of total skin extracts of healthy mouse skin (FIG. 11), healthy skin from a human skin cancer patient (FIG. 12) as well as psoriatic skin from a human psoriasis patient (FIG. 13) with the salt of Etomoxir resulted in a dose-dependent reduction CPT1 activity.

Figure 17:
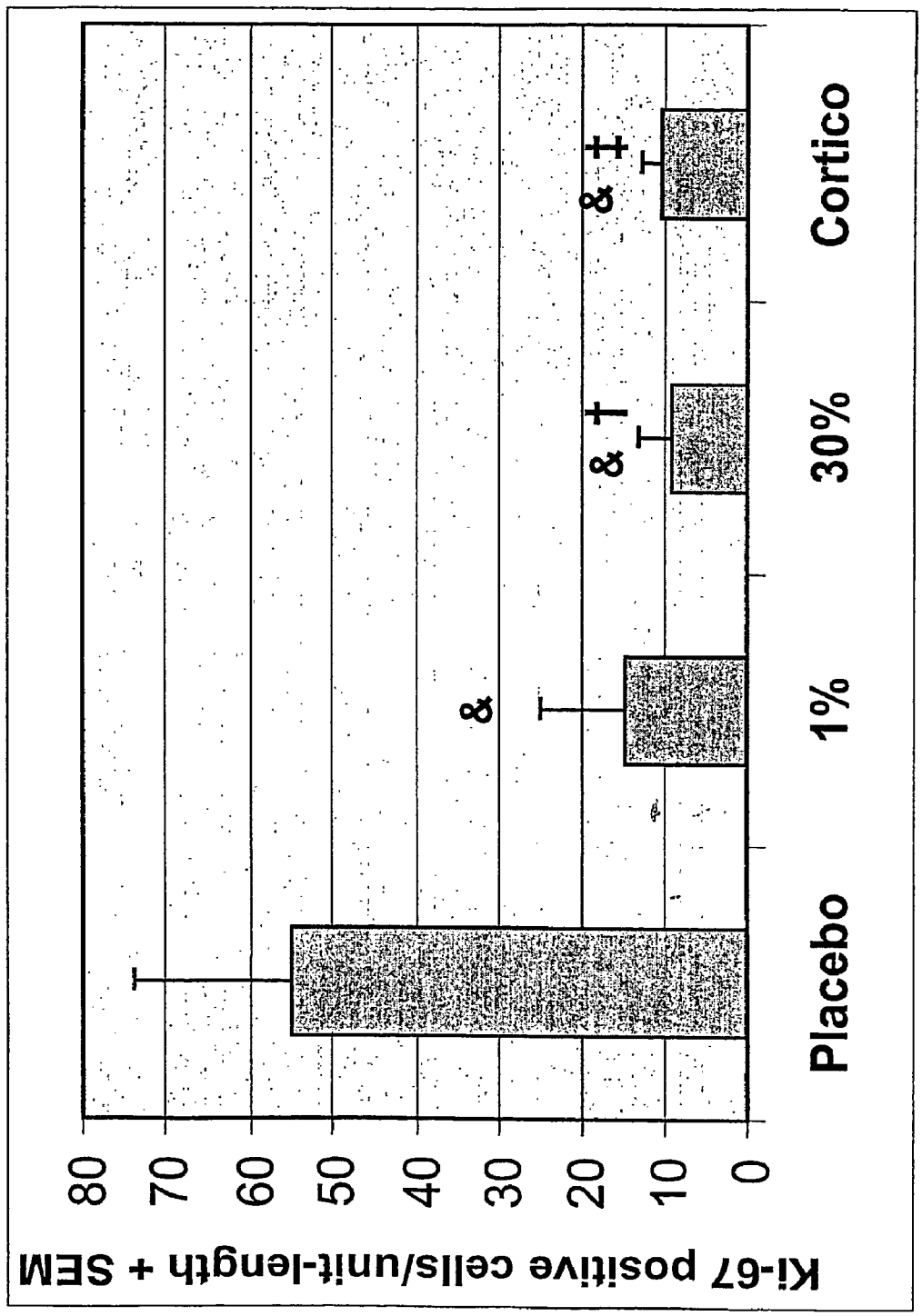
FIG. 17: Effect of treatment with Etomoxir on the number of (Ki-67 positive) proliferating cells of transplanted human psoriasis skin.
& $P<0.001$ and $P=0.001$(1%) as compared to placebo
†$P=0.006$ as compared to 1%
‡$P=0.009$ as compared to 1%
Figure 18:
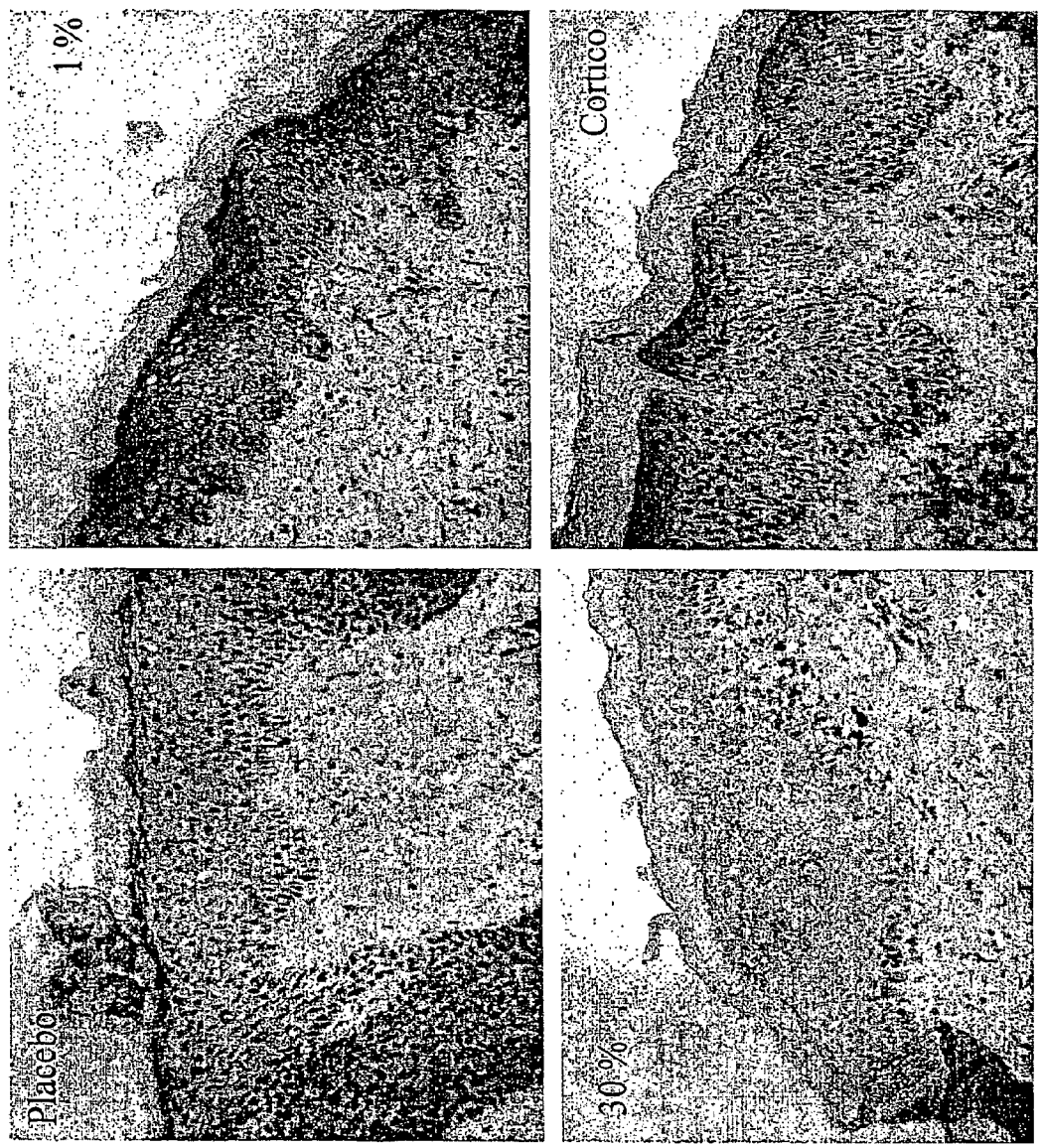
FIG. 18: Microscopic pictures of the effect of treatment with Etomoxir on the differentiation rate (distribution of ULEX) of transplanted human psoriasis skin.
Figure 19:
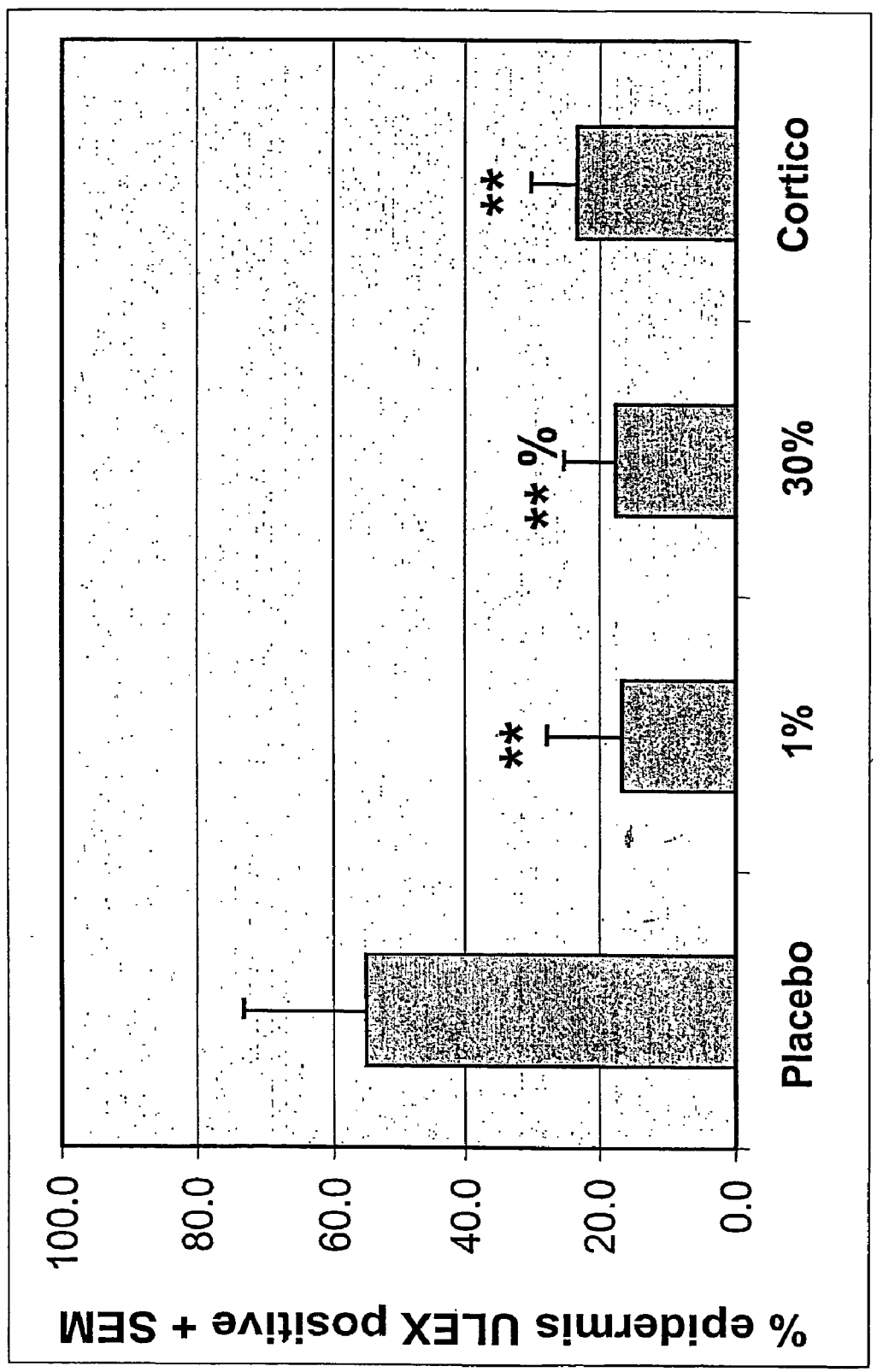
FIG. 19: Effect of treatment with Etomoxir on the differentiation rate (distribution of ULEX) of transplanted human psoriasis skin.
** $P<0.001$ and $P=0.001$ (1%) as compared to placebo
% $P=0.034$ as compared to 1%

Epidermal Thickness, Number of Ki67 Positive Cells and the Percentage of ULEX-positive Cells Treatment with placebo resulted in an average epidermal thickness of 138±24 μm (FIGS. 14 and 15) and a proliferation rate (Ki-67) of 55±37 positive cells/unit-length (FIGS. 16 and 17) and a percentage of ULEX-positive cells in the epidermis of 55±19% (FIGS. 18 and 19).

Figure 14:
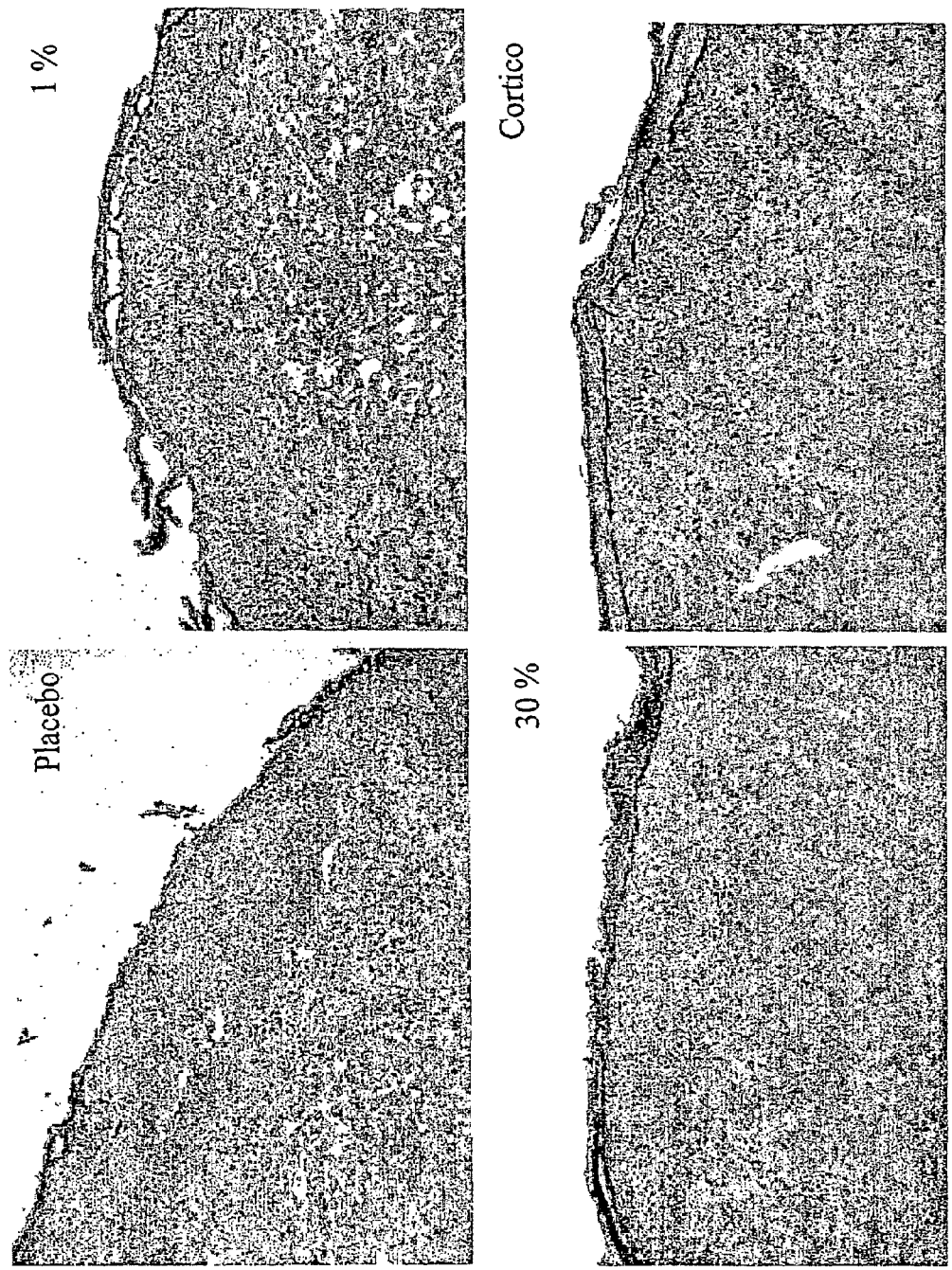
FIG. 14: Microscopic pictures of the effect of treatment with Etomoxir on the epidermal thickness of transplanted human psoriasis skin.
Figure 15:
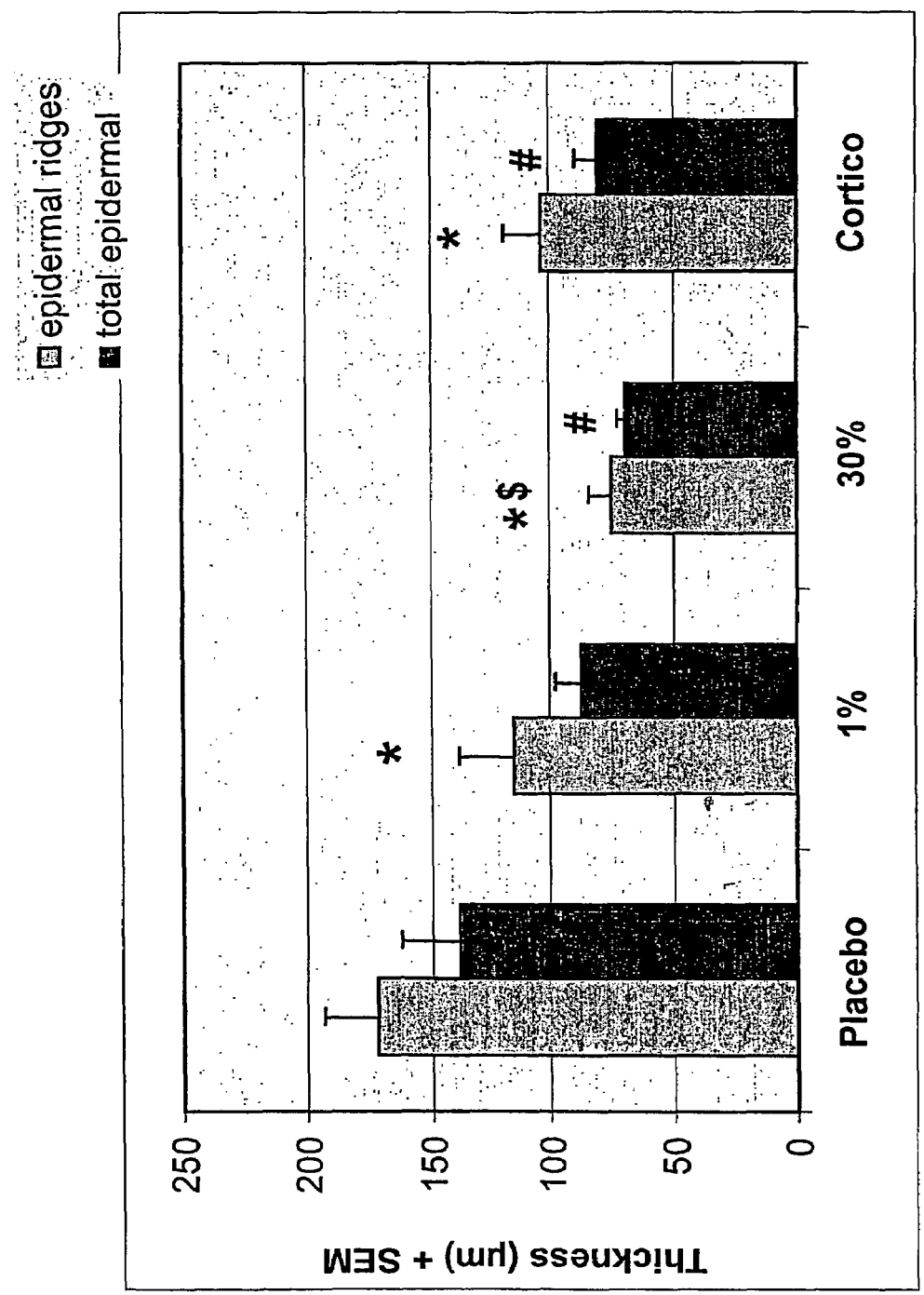
FIG. 15: Effect of treatment with Etomoxir on the epidermal thickness of transplanted human psoriasis skin. In this figure the average epidermal thickness measurements for both the ridges (including epidermal ridges only) and the average of the total epidermis are presented.
* $P<0.001$ as compared to placebo
$ $P=0.014$ as compared to 1%
$P=0.005$ (30%) and $P=0.017$ (Cortico) as compared to placebo
Figure 16:
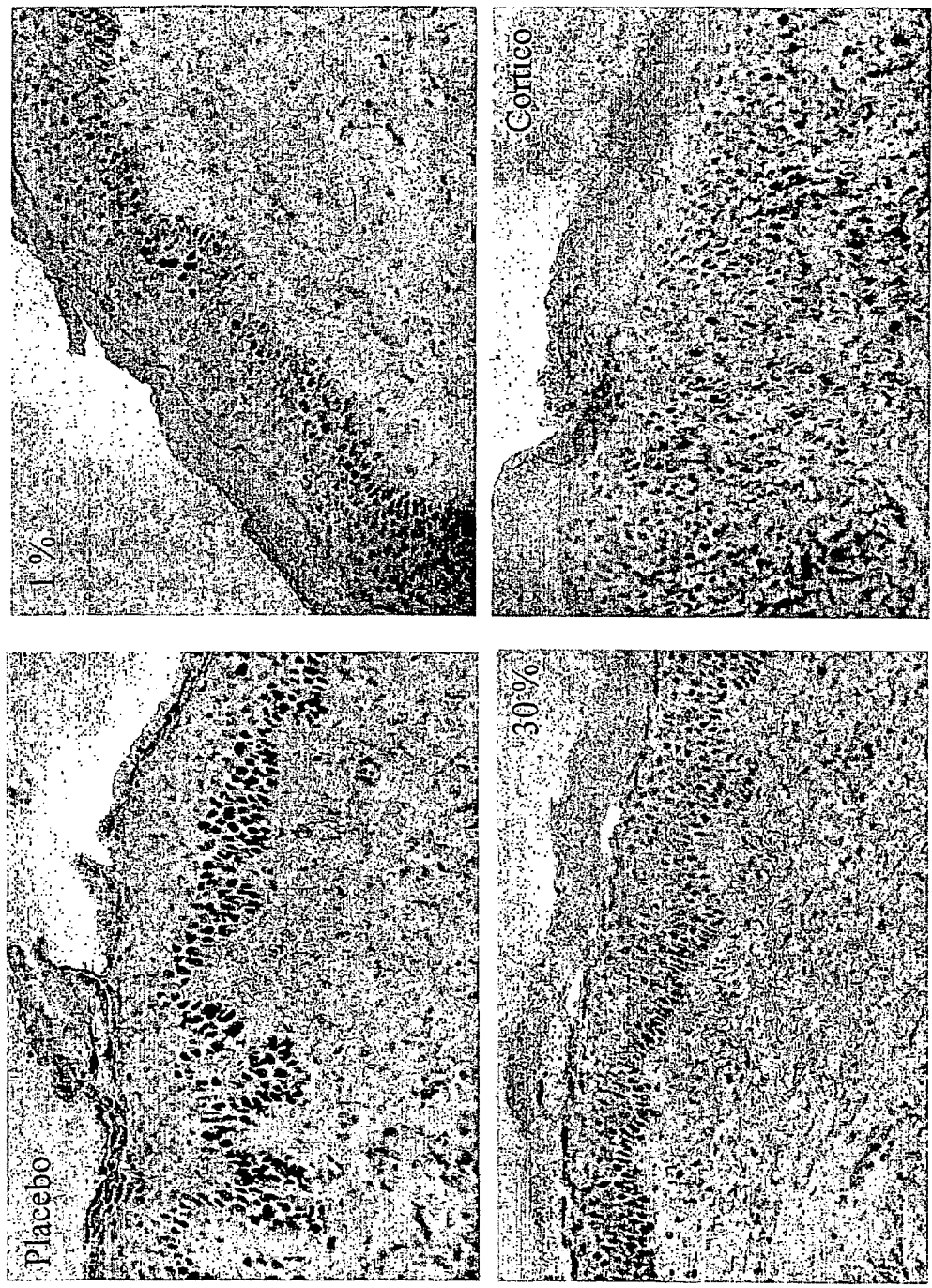
FIG. 16: Microscopic pictures of the effect of treatment with Etomoxir on the number of (Ki-67 positive) proliferating cells of transplanted human psoriasis skin.

Treatment with the positive control (corticosteroid group) showed a significant reduction of the average epidermal thickness of 81±9 μm (FIGS. 14 and 15). The number of Ki67 positive cells showed also a significant decrease of 10±6 positive cells/unit-length (FIGS. 16 and 17). Finally, treatment with corticosteroid showed a significant lower percentage of ULEX-positive cells in the epidermis of 24±7% (FIGS. 18 and 19) as compared to the placebo group.

The epidermises of the three mice treated with 30% Etomoxir and three remaining mice treated with 1% Etomoxir, for which there were reliable data, showed a significant reduction in thickness of 69±4 μm and 88±10 μm, respectively, when compared to the placebo group (FIGS. 14 and 15). The reductions in epidermal thickness were comparable to those observed when transplants were treated with the positive control (corticosteroid group; FIGS. 14 and 15). Treatment with Etomoxir (both 30 and 1%) showed a significant decrease in number of Ki67 positive cells as compared to the placebo group (FIGS. 16 and 17).

Finally, treatment with Etomoxir (both 30 and 1%) showed a significantly lower percentage of ULEX-positive cells in the epidermis (differentiation rate) of respectively 18±8% and 17±11% (FIGS. 18 and 19) as compared to the placebo group.

EXAMPLE 2

Figure 21:
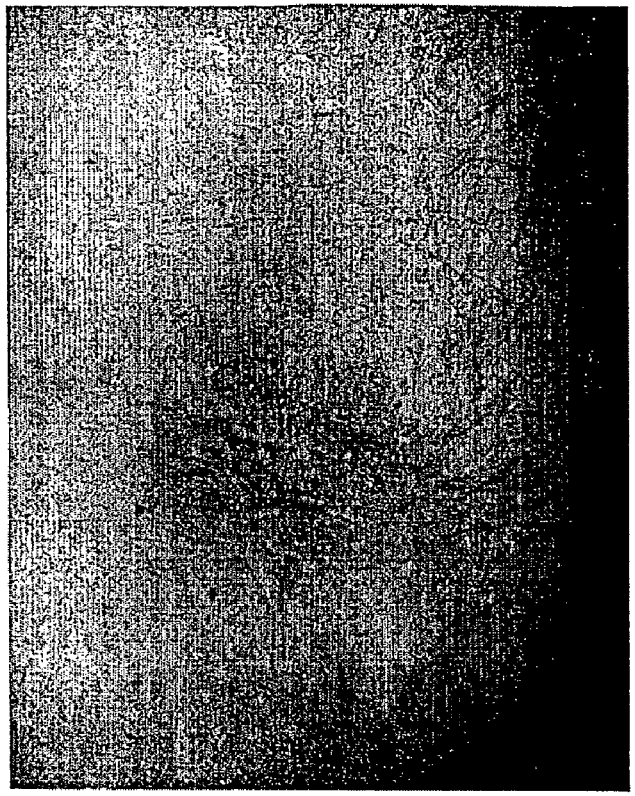
FIG. 21.
Figure 21:
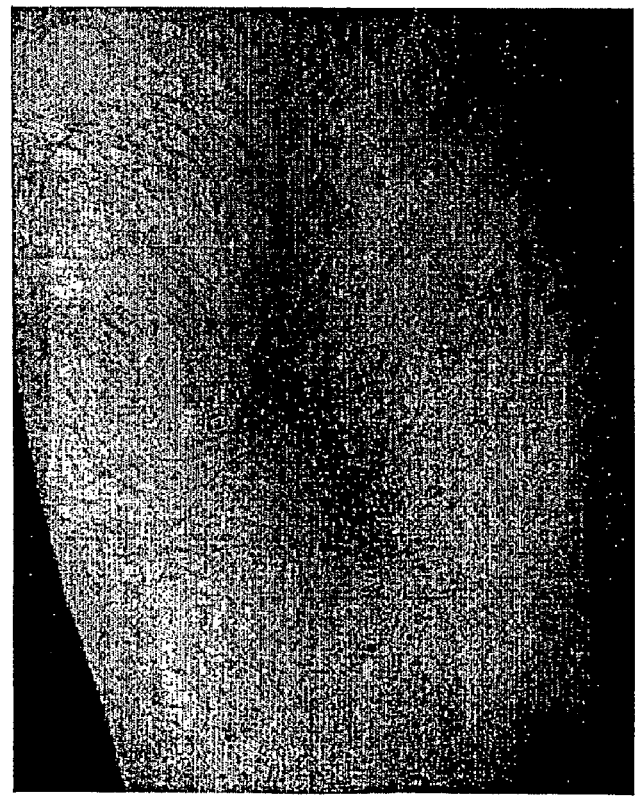

Two psoriatic lesions were treated, each on one inside of the elbow of a test person, one with placebo (pure Vaseline)

and corticosteroid creme and the other with verum (250 mg Etomoxir per g Vaseline) and corticosteroid creme (betamethason-17-valerat 1.22 mg/g). Verum or placebo as well as corticosteroid creme were applied once a day for a treatment period of three weeks. After the treatment, the following effects were observed: The Etomoxir/corticosteroid treated lesion as well as the placebo/corticosteroid treated lesion disappeared during the treatment period. However, after stopping the treatment, the Etomoxir/corticosteroid treated lesion did not recur within the observation period of 6 months, while the placebo/corticosteroid treated lesion recurred within 2 weeks (see FIG. 21).

The invention claimed is:

1. A method of treating psoriasis in a patient in need thereof by administering 2-(6-(4-chlorophenoxy)hexyl)oxirane-2-carboxylic acid ethyl ester (Etomoxir) to a patient in a pharmacologically effective amount.

2. The method according to claim 1, wherein the patient is human.

3. The method according to claim 1, wherein the 2-(6-(4-chlorophenoxy)hexyl)oxirane-2-carboxylic acid ethyl ester is administered topically.

4. The method according to claim 1, wherein the 2-(6-(4-chlorophenoxy)hexyl)oxirane-2-carboxylic acid ethyl ester is administered together with at least one excipient and/or auxiliary.

5. The method according to claim 4, wherein the excipient and/or auxiliary is selected from the group consisting of one or more suitable adjuvant(s), one or more pharmaceutically active and/or acceptable carrier(s), diluent(s), filler(s), binder(s), disintegrant(s), lubricant(s), glident(s), coloring agent(s), flavoring agent(s), opaquing agent(s) and plasticizer(s).

6. The method according to claim 4, wherein the 2-(6-(4-chlorophenoxy)hexyl)oxirane-2-carboxylic acid ethyl ester is administered topically and the said at least one excipient and/or auxiliary is hydrophobic and is selected from the group consisting of petroleum jelly, wax, oleyl alcohol, propylene glycol monostearate, propylene glycol monopalmitostearate, isopropyl laureate, isopropyl myristate, isopropyl palmitate, isopropyl stearate, ethyl myristate, propyl myristate, butyl myristate, ethyl oleate, Cetylstearyl alcohol, lanolin alcohol and paraffin oil.

* * * * *